(12) United States Patent
Fu et al.

(10) Patent No.: US 11,892,457 B2
(45) Date of Patent: Feb. 6, 2024

(54) PROTEOLIPOSOME-BASED ZNT8 SELF-ANTIGEN FOR TYPE 1 DIABETES DIAGNOSIS

(71) Applicants: THE JOHNS HOPKINS UNIVERSITY, Baltimore, MD (US); The Board of Trustees of the Leland Stanford Junior University, Stanford, CA (US)

(72) Inventors: Dax Fu, Short Hills, NJ (US); Chengfeng Merriman, Essex, MD (US); Hongjie Dai, Stanford, CA (US); Hao Wan, Stanford, CA (US)

(73) Assignees: The Johns Hopkins University, Baltimore, MD (US); The Board of Trustees of the Leland Stanford Junior University, Stanford, CA (US)

( * ) Notice: Subject to any disclaimer, the term of this patent is extended or adjusted under 35 U.S.C. 154(b) by 117 days.

(21) Appl. No.: 16/629,054

(22) PCT Filed: Jul. 5, 2018

(86) PCT No.: PCT/US2018/040890
§ 371 (c)(1),
(2) Date: Jan. 7, 2020

(87) PCT Pub. No.: WO2019/014044
PCT Pub. Date: Jan. 17, 2019

(65) Prior Publication Data
US 2020/0132698 A1    Apr. 30, 2020

Related U.S. Application Data

(60) Provisional application No. 62/531,525, filed on Jul. 12, 2017.

(51) Int. Cl.
*G01N 33/68* (2006.01)
*G01N 33/564* (2006.01)
*G01N 21/64* (2006.01)

(52) U.S. Cl.
CPC ..... *G01N 33/6893* (2013.01); *G01N 21/6428* (2013.01); *G01N 33/564* (2013.01); *G01N 2021/6439* (2013.01); *G01N 2800/042* (2013.01)

(58) Field of Classification Search
CPC ....... G01N 2021/6439; G01N 21/6428; G01N 2800/042; G01N 33/564; G01N 33/6893
See application file for complete search history.

(56) References Cited

U.S. PATENT DOCUMENTS

| | | |
|---|---|---|
| 4,399,216 A | 8/1983 | Axel et al. |
| 4,634,665 A | 1/1987 | Axel et al. |
| 4,880,935 A | 11/1989 | Thorpe |
| 5,122,368 A | 6/1992 | Greenfield et al. |
| 5,179,017 A | 1/1993 | Axel et al. |
| 5,225,539 A | 7/1993 | Winter |
| 5,399,363 A | 3/1995 | Liversidge et al. |
| 5,466,468 A | 11/1995 | Schneider et al. |
| 5,530,101 A | 6/1996 | Queen et al. |
| 5,543,158 A | 8/1996 | Greg et al. |
| 5,580,579 A | 12/1996 | Ruddy et al. |
| 5,585,089 A | 12/1996 | Queen et al. |
| 5,613,308 A | 3/1997 | Little |
| 5,622,929 A | 4/1997 | Willner et al. |
| 5,624,821 A | 4/1997 | Winter et al. |
| 5,629,001 A | 5/1997 | Michael et al. |
| 5,641,515 A | 6/1997 | Ramtoola |
| 5,641,640 A | 6/1997 | Hanning |
| 5,725,871 A | 3/1998 | Illum |
| 5,731,168 A | 3/1998 | Carter et al. |
| 5,756,353 A | 5/1998 | Debs |
| 5,780,045 A | 7/1998 | McQuinn et al. |
| 5,792,451 A | 8/1998 | Sarubbi et al. |
| 5,804,212 A | 9/1998 | Illum |
| 5,824,805 A | 10/1998 | King et al. |
| 5,834,597 A | 11/1998 | Tso et al. |
| 5,859,205 A | 1/1999 | Adair et al. |
| 5,869,046 A | 2/1999 | Presta et al. |
| 5,892,019 A | 4/1999 | Schlom et al. |
| 6,165,710 A | 12/2000 | Robinson |
| 6,214,345 B1 | 4/2001 | Firestone et al. |
| 6,407,213 B1 | 6/2002 | Carter et al. |

(Continued)

FOREIGN PATENT DOCUMENTS

| | | |
|---|---|---|
| CN | 101646781 | 2/2010 |
| CN | 106084043 | 11/2016 |

(Continued)

OTHER PUBLICATIONS

Bogdanov et al., "Lipids and topological rules governing membrane protein assembly," Biochim. Biophys. Acta, 2014, vol. 1843, issue 8, pp. 1475-1488.*
Wan et al., "Proteoliposome-based full-length ZnT8 self-antigen for type 1 diabetes diagnosis on a plasmonic platform," PNAS, Sep. 19, 2017, vol. 114, No. 38, pp. 10196-10201 (IDS submitted Jan. 13, 2023); Supporting Information, pp. 1-10.*
Wenzlau, J., "Novel Diabetes Autoantibodies and Prediction of Type 1 Diabetes" Curr Diab Rep. Oct. 2013 ; 13(5): . doi:10.1007/s11892-013-0405-9.
Wahl, G., "Molecular hybridization of immobilized nucleic acids: theoretical concepts and practical considerations" Methods in Enzymology, vol. 152 (1987).

(Continued)

*Primary Examiner* — Galina M. Yakovleva
(74) *Attorney, Agent, or Firm* — Fish & Richardson P.C.

(57) ABSTRACT

Methods of detecting ZNT8 antibodies in serum are described. The methods include proteoliposomes comprising a transmembrane domain (TMD) and a cytosolic domain (CTD) of ZnT8 proteins exposed on the exterior of the proteoliposome; serum comprising antibodies targeting the ZnT8 proteins; and labelled captured autoantibodies that bind to ZnT8 antibodies.

16 Claims, 5 Drawing Sheets
Specification includes a Sequence Listing.

(56) References Cited

U.S. PATENT DOCUMENTS

| | | |
|---|---|---|
| 6,613,308 B2 | 9/2003 | Bartus et al. |
| 6,737,514 B1 | 5/2004 | Wang |
| 6,881,557 B2 | 4/2005 | Foote |
| 8,563,291 B2 | 10/2013 | Yoshimura et al. |
| 9,568,482 B2 | 2/2017 | Seve et al. |
| 11,016,085 B2 | 5/2021 | Fu |
| 2009/0186364 A1* | 7/2009 | Yoshimura ....... G01N 33/56983 435/7.1 |
| 2009/0191574 A1 | 7/2009 | Halperin |
| 2010/0068199 A1 | 3/2010 | Liang |
| 2010/0158909 A1 | 6/2010 | McDonagh et al. |
| 2012/0238572 A1 | 9/2012 | Su et al. |
| 2016/0025744 A1* | 1/2016 | Feldman .......... G01N 33/54373 506/9 |
| 2017/0096497 A1 | 4/2017 | Weisbart |
| 2018/0243408 A1 | 8/2018 | Fanger et al. |
| 2019/0137485 A1 | 5/2019 | Fu |
| 2021/0263021 A1 | 8/2021 | Fu |

FOREIGN PATENT DOCUMENTS

| | | |
|---|---|---|
| CN | 106084051 | 11/2016 |
| CN | 106771233 | 5/2017 |
| EP | 404097 | 12/1990 |
| WO | WO 198705330 | 9/1987 |
| WO | WO 198912624 | 12/1989 |
| WO | WO 199311161 | 6/1993 |
| WO | WO 2008083331 | 7/2008 |
| WO | WO 2012062697 | 5/2012 |
| WO | WO 2012173184 | 12/2012 |
| WO | 2013/071055 A1 | 5/2013 |
| WO | WO 2014142517 | 9/2014 |
| WO | WO 2014160175 | 10/2014 |
| WO | WO 2017189483 | 11/2017 |
| WO | WO 2019014044 | 1/2019 |
| WO | WO 2020037174 | 2/2020 |
| WO | WO 2020247920 | 12/2020 |

OTHER PUBLICATIONS

Kimmel, A., "Identification and characterization of specific clones: strategy for confirming the validity of presumptive clones" Methods in Enzymology, vol. 152 (1987).
Delic-Sarac, M, et al. (2016) ELISA Test for Analyzing of Incidence of Type 1 Diabetes Autoantibodies (GAD and IA2) in Children and Adolescents. Acta Inform Med 24:61-65.
Grunstein, M., et al., "Colony hybridization: a method for the isolation of cloned DNAs that contain a specific gene" Proc.Nat. Acad.Sci. USA, vol. 72, No. 10, pp. 3961-3965, (1975).
Sosenko, J. M, et al. (2017) The Use of Electrochemiluminescence Assays to Predict Autoantibody and Glycemic Progression Toward Type 1 Diabetes in Individuals with Single Autoantibodies. Diabetes Technol Ther 3:183-187.
Tiberti, C, et al. (2011) Detection of four diabetes specific autoantibodies in a single radioimmunoassay: an innovative high-throughput approach for autoimmune diabetes screening. Clin Exp Immunol 3:317-324.
Jaraosz-Chobot, P., et al. (2011) Rapid increase in the incidence of type 1 diabetes in Polish children from 1989 to 2004, and predictions for 2010 to 2025. Diabetologia 54:508-515.
Wenzlau, J, et al. (2007) The cation efflux transporter ZnT8 (Slc30A8) is a major autoantigen in human type 1 diabetes. Proc Natl Acad Sci USA 43:17040-17045.
Darmon, A., et al., "Oriented reconstitution of red cell membrane proteins and assessment of their transmembrane disposition by immunoquenching of fluorescence" Biochimica et Biophysica Acta 817 (1985) pp. 238-248.
Chimienti, F, et al. (2014) Identification and cloning of a beta-cell-specific zinc transporter, ZnT-8, localized into insulin secretory granules. Diabetes 53:2330-2337.

Lu, M, et al. (2009) Structural basis for autoregulation of the zinc transporter YiiP. Nat Struct Mol Biol 16:1063-1067.
Lemaire, K, et al. (2009) Insulin crystallization depends on zinc transporter ZnT8 expression, but is not required for normal glucose homeostasis in mice. Proc Natl Acad Sci U S A 106:14872-14877.
Huang, Q, et al. (2017) Coupling of Insulin Secretion and Display of a Granule-resident Zinc Transporter ZnT8 on the Surface of Pancreatic Beta Cells. J Biol Chem 292:4034-4043.
Zhang, et al. (2017) Diagnosis of Zika virus infection on a nano-technology platform. Nat Med 23:548-550.
Tabakman, S, et al. (2011) Plasmonic substrates for multiplexed protein microarrays with femtomolar sensitivity and broad dynamic range. Nat Commun DOI: 10.1038/ncomms1477.
Zhang, B, et al. (2013) A plasmonic chip for biomarker discovery and diagnosis of type 1 diabetes. Nat Med 20:948-953.
Li, X, et al. (2016) Multiplexed Anti-Toxoplasma IgG, IgM and IgA Assay on Plasmonic Gold Chips: Towards Making Mass Screening Possible with Dye Test Precision. J Clin Microbiol 54:1684-1685.
Burbelo, P, et al. (2015) Luciferase Immunoprecipitation Systems for Measuring Antibodies in Autoimmune and Infectious Diseases. Transl Res 165:325-335.
Wan, H., et al., "Proteoliposome-based full-length ZnT8 self-antigen for type 1 diabetes diagnosis on a plasmonic platform" PNAS Sep. 19, 2017; vol. 114, No. 38, pp. 10196-10201.
Davidson, H. W, et al. (2014) Zinc transporter 8 (ZnT8) and beta cell function. Trends Endocrinol Metab 25:415-424.
Wenzlau, J. M, et al. (2008) A common nonsynonymous single nucleotide polymorphism in the SLC30A8 gene determines ZnT8 autoantibody specificity in type 1 diabetes. Diabetes 57:2693-2697.
Merriman, C., et al., (2016) "Lipid-tuned Zinc Transport Activity of Human ZnT8 Protein Correlates with Risk for Type-2 Diabetes" J Biol Chem 291:26950-26957.
Cheng, L, et al. (2015) "Prokaryotic Expression of Bioactive Zinc Transporter 8 Antigens and Detection of Diabetes Specific Autoantibodies in a Single Dot Immunogold Filtration Assay" Clin Lab 10:1445-1452.
Abdiche et al "Determining Kinetics and Affinities of Protein Interactions Using a Parallel Real-time Label-free Biosensor the Octet," Analytical Biochemistry, 2008, 377:209-217.
Akerfeldt et al., "Cytokine-induced beta-cell death is independent of endoplasmic reticulum stress signaling," Diabetes, 2008, 57(11):3034-3044.
Aplin et al., "Preparation, Properties, and Applications of Carbohydrate Conjugates of Proteins and Lipids," CRC Crit. Rev. Biochem., May 1981, 22:259-306.
Arnon et al, "Monoclonal Antibodies For Immunotargeting Of Drugs In Cancer Therapy," Monoclonal Antibodies And Cancer Therapy, 1986, pp. 243-256.
Arvan et al., "Islet autoantigens: structure, function, localization, and regulation," Cold Spring Harb Perspect Med , Aug. 2012, 2(8):a007658.
Ashcroft et al., "Diabetes mellitus and the B cell: the last ten years," Cell, Mar. 16, 2012, 148(6):1160-71.
Atkinson et al., "How does type 1 diabetes develop?: the notion of homicide or beta-cell suicide revisited," Diabetes, 2011, 60(5):1370-1379.
Barelle et al., "VNARs: An Ancient and Unique Repertoire of Molecules That Deliver Small, Soluble, Stable and High Affinity Binders of Proteins," Antibodies, 2015, 4(3):240-258.
Barlow et al., "Novel insights into pancreatic beta-cell glucolipotoxicity from real-lime functional analysis of mitochondrial energy metabolism in INS-1E insulinoma cells," Biochem J, 2013, 456(3):417-426.
Benton et al., "creening lambdagt recombinant clones by hybridization to single plaques in situ," Science, Apr. 1977, 196(4286):180-182.
Berge et al., "Pharmaceutical salts," J. Pharm. Sci. Jan. 1977, 66(1):1-19.
Better et al., "*Escherichia coli* secretion of an active chimeric antibody fragment," Science, May 1988, 240(4855):1041-1043.
Better et al., "Expression of Engineered Antibodies and Antibody Fragments in Microorganisms," Methods in Enzymology, 1989, 178:476-496.

(56) References Cited

OTHER PUBLICATIONS

Bindels et al., "mScarlet: a bright monomeric red fluorescent protein for cellular imaging," Nat Methods, 2017, 14:53-56.
Bird et al., "Single chain antibody variable regions," Trends in Biotechnology, Jan. 1991, 9:132-137.
Bird et al., "Single-Chain Antigen-Binding Proteins," Science, 1988, 242(4877):423-426.
Bloem et al., "The elusive role of B lymphocytes and islet autoantibodies in (human) type 1 diabetes," Diabetologia, 2017, 60:1185-1189.
Boesgaard et al., "The common SLC30A8 Arg325Trp variant is associated with reduced first-phase insulin release in 846 non-diabetic offspring of type 2 diabetes patients—the EUGENE2 study," Diabetologia, May 2008, 51(5):816-20.
Bonneford et al., "Rare and common genetic events in type 2 diabetes: what should biologists know?" Cell Metab, Mar. 2015, 21(3):357-68.
Bonner-Weir et al., "New perspectives on the microvasculature of the islets of Langerhans in the rat," Diabetes, 1982, 31(10):883-889.
Brenner et al., "Encoded combinatorial chemistry," Proc. Natl. Acad. Sci. USA. Jun. 1992, 89(12):5381-5383.
Busch et al., "Increased fatty acid desaturation and enhanced expression of stearoyl coenzyme A desaturase protects Jancreatic beta-cells from lipoapoptosis," Diabetes, 2005, 54(10):2917-2924.
Butcher et al., "Association of proinflammatory cytokines and islet resident leucocytes with islet dysfunction in type 2 dliabetes," Diabetologia, 2014, 57(3):491-501.
Carell et al., "New promise in combinatorial chemistry: synthesis, characterization, and screening of small-molecule libraries in solution," Chem. Biol. 1995, 2(3):171-183.
Carter et al., "High level *Escherichia coli* expression and production of a bivalent humanized antibody fragment," Biotechnology, 1992, 10(2):163-167.
Chabosseau et al., "Mitochondrial and ER-targeted eCALWY probes reveal high levels of free Zn2+," ACS Chem Biol, 2014, 9:2111-2120.
Chabosseau et al., "Zinc and diabetes, Arch Biochem Biophys," 2016, 611:79-85.
Chao et al., "Kinetic Study of the Antiport Mechanism of an *Escherichia coli* Zinc Transporter, ZitB," J Biol Chem, 2004, 279(13):12043-12050.
Chatterjee et al., "Type 2 diabetes," Lancet, Jun. 2017, 389(10085):2239-2251.
Cheng et al., "Tumor necrosis factor alpha-induced protein-3 protects zinc transporter 8 against proinflammatory cytokine-induced downregulation," Exp Ther Med, 2016, 12:1509-1514.
Cherezov et al., "Insights into the mode of action of a putative zinc transporter CzrB in Thermus thermophilus," Structure, Sep. 2008, 16(9):1378-88.
Chimienti et al., "In vivo expression and functional characterization of the zinc transporter Zn TB in glucose-induced nsulin secretion," J Cell Sci, Oct. 2006, 119(Pt 20):4199-4206.
Chimienti, "Zinc, pancreatic islet cell function and diabetes: new insights into an old story," Nutr Res Rev, 2013, 26:1-11.
Cieslak et al., "Role of proinflammatory cytokines of pancreatic islets and prospects of elaboration of new methods for the diabetes treatment," Acta Biochim Pol, 2015, 62(1):15-21.
Cnop et al., "Mechanisms of pancreatic beta-cell death in type 1 and type 2 diabetes: many differences, few imilarities," Diabetes, 2005, 54(Suppl 2):S97-107.
Co et al., "A humanized antibody specific for the platelet integrin gpIIb/IIIa," J Immunol, 1994, 152(6):2968-2976.
Corbin et al., "A Practical Guide to Rodent Islet Isolation and Assessment Revisited," Biol Proced Online, 2021, 23(1):7.
Cwirla et al., "Peptides on phage: a vast library of peptides for identifying ligands," Biochemistry 1990, 87(16):6378-6382.
Darling et al., "Kinetic exclusion assay technology: characterization of molecular interactions," Assay and Drug Dev Tech, 2004, 2(6):647-657.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody," J. Immunol, 2002, 169(6):3076-3084.
Degorce et al., "HTRF: A technology tailored for drug discovery—a review of theoretical aspects and recent applications," Curr Chem Genomics, May 28, 2009, 3:22-32.
Dodson et al., "The role of assembly in insulin's biosynthesis," Curr Opin Struct Biol, 1998, 8(2):189-194.
Donath et al., "Type 2 diabetes as an inflammatory disease," Nat Rev Immunol, 2011, 11(2):98-107.
Dubowchik et al., "Receptor-mediated and enzyme-dependent targeting of cytotoxic anticancer drugs," Pharm. Therapeutics, Aug. 1999, 83(2):67-123.
Dudek et al., "Constitutive and inflammatory immunopeptidome of pancreatic beta-cells," Diabetes, 2012, 61(11):3018-3025.
Dunn, "Zinc-ligand interactions modulate assembly and stability of the insulin hexamer—a review," Biometals, Aug. 2005, 18(4):295-303.
Dwivedi et al., "Loss of ZnT8 function protects against diabetes by enhanced insulin secretion," Nat Genet, 2019, 51:1596-1606.
Edge et al., "Deglycosylation of Glycoproteins by Trifluoromethanesulfonic Acid," Anal. Biochem., 1981, 118:131-137.
Egefjord et al., "Zinc transporter gene expression is regulated by pro-inflammatory cytokines: a potential role for inc transporters in beta-cell apoptosis?" BMC Endocr Disord, 2009, 7(9).
Eide, "The oxidative stress of zinc deficiency," Metallomics, 2011, 3(11):1124-1129.
Eizirik et al., "The role of inflammation in insulitis and beta-cell loss in type 1 diabetes," Nat Rev Endocrinol, 2009, 5(4):219-226.
El Muayed et al., "Acute cytokine-mediated downregulation of the zinc transporter ZnT8 alters pancreatic beta-cell unction," J Endocrinol, 2010, 206 (2):159-169.
El-Gohary et al., "Three-dimensional analysis of the islet vasculature," Anat Rec (Hoboken), 2012, 295:1473-1481.
Enee et al., "ZnTB is a major COB+ T cell-recognized autoantigen in pediatric type 1 diabetes, Diabetes," 2012, 61(7):1779-1784.
Eriksson et al., "Pancreatic imaging using an antibody fragment targeting the zinc transporter type 8: a direct comparison with radio-iodinated Exendin-4," Acta Diassbetol, 2018, 55(1):49-57.
Extended European Search Report in European Application No. 19849457.7, dated Jul. 13, 2022, 14 pages.
Fabregat et al., "The Reactome Pathway Knowledgebase," Nucleic Acids Res, 2018, 46(D1):D649-D655.
Farino et al., "Development of a Rapid Insulin Assay by Homogenous Time-Resolved Fluorescence," PLoS One,2016, 11(2):e0148684.
Felder, "The Challenge of Preparing and Testing Combinatorial Compound Libraries in the Fast Lane, at the Front end of Drug Development,," Chimia 1994, 48:512-541.
Ferrannini et al., "Progression to diabetes in relatives of type 1 diabetic patients: mechanisms and mode of onset," Diabetes, 2010, 59(3):679-685.
Flannick et al., "Exome sequencing of 20,791 cases of type 2 diabetes and 24,440 controls," Nature, 2019, 570(7759):71-76.
Flannick et al., "Loss-of-function mutations in SLC30A8 protect against type 2 diabetes," Nat Genet, 2014, 46(4):357-363.
Fonseca et al., "Endoplasmic reticulum stress in beta-cells and development of diabetes," Curr Opin Pharmacol, 2009, 9(6):763-770.
Foster et al., "Elemental composition of secretory granules in pancreatic islets of Langerhans," Biophys J, 1993, 64(2):525-532.
Fred et al., "Role of the AMP kinase in cytokine-induced human EndoC-belaH1 cell death, Mol Cell Endocrinol," 2015, 414:53-63.
Friend, et al., "Translational genomics. Clues from the resilien," Science, May 2014, 344(6187):970-2.
Fukuda et al., "In vitro evolution of single-chain antibodies using mRNA display," Nucleic Acids Res., Oct. 2006, 34(19):e127.
Gallop et al, "Applications of combinatorial technologies to drug discovery. 1. Background and peptide combinatorial libraries," J. Med. Chem., 1994, 37(9):1233-1251.
Garner, "Na,K-ATPase in the nuclear envelope regulates Na+: K+ gradients in hepatocyte nuclei," J Membr Biol, 2002, 187:97-115.

(56) References Cited

OTHER PUBLICATIONS

Geertsma et al., "Membrane reconstitution of ABC transporters and assays of translocator function," Nature Protocols, 2008, 3(2):256-266.
Ghazalpour et al., "Comparative analysis of proteome and transcriptome variation in mouse," PLoS Genet, 2011, 7:e1001393.
Ghetie et al., "Multiple roles for the major histocompatibility complex class I-related receptor FcRn," Annu. Rev. Immunol., 2000, 18:739-766.
Ghetie et al., "Transcytosis and catabolism of antibody," Immunol. Res., 2002, 25(2):97-113.
Gordon et al., "Applications of Combinatorial Technologies to Drug Discovery. 2. Combinatorial Organic Synthesis, Library Screening Strategies, and Future Directions," J Med. Chem. 1994, 37(10):1385-1401.
Gu et al., "Novel autoantibodies to the beta-cell surface epitopes of ZnT8 in patients progressing to type-1 diabetes," J Autoimmun, 2021, 122:102677.
Gupta et al., "Visualizing the kinetic power stroke that drives proton-coupled zinc(II) transport," Nature, 2014, 512:101-104.
Gurgul-Convey et al., "Sensitivity profile of the human EndoC-betaH1 beta cell line to proinflammatory cytokines," Diabetologia, 2016, 59(10):2125-2133.
Hahn et al., "3D imaging of human organs with micrometer resolution—applied to the endocrine pancreas," Commun Biol, 2021, 4:1063.
Hakonen et al., "MANF protects human pancreatic beta cells against stress-induced cell death," Diabetologia, 2018, 61(10):2202-2214.
Hara et al., "Transgenic mice with green fluorescent protein-labeled pancreatic beta-cells," Am J Physiol Endocrinol Metab, 2003, 284:E177-183.
Hieter et al., "Evolution of Human Immunoglobulin kappa J region genes," J. Biol. Chem., 1982, 257:1516-1522.
Hinton et al., "Engineered human IgG antibodies with longer serum half-lives in primates," J. Biol. Chem., Feb. 2004, 279(8):6213-6216.
Ho et al, Gene, "Site-directed mutagenesis by overlap extension using the polymerase chain reaction." Apr. 1989, 77(1):51-59.
Hoch et al., "Histidine pairing at the metal transport site of mammalian ZnT transporters controls Zn2+ over Cd2+ selectivity," Proc Natl Acad Sci U S A, May 2012, 109(19):7202-7.
Holliger et al., "Diabodies': small bivalent and bispecific antibody fragments," Proc. Natl. Acad. Sci. U S A., Jul. 1993, 90:6444-6448.
Homma et al., "SOD1 as a molecular switch for initiating the homeostatic ER stress response under zinc deficiency," Mol Cell, 2013, 52(1):75-86.
Hotamisligil et al., "Inflammation, metaflammation and immunometabolic disorders," Nature, 2017, 542(7640):177-185.
Houghten et al., "Generation and use of synthetic peptide combinatorial libraries for basic research and drug discovery," Nature, 1991, 354:84-86.
Houghten, "Peptide libraries: criteria and trends," Trends Genet, 1993, 9:235-239.
Huang, "Zinc and its transporters, pancreatic beta-cells, and insulin metabolism," Vitarn Horm, 2014, 95:365-390.
Hudson, et al., "High avidity scFv multimers; diabodies and triabodies," J Immunol. Methods, Dec. 1999, 231(1-2):177-189.
Huston et al., "Protein engineering of antibody binding sites: recovery of specific activity in an anti-digoxin single-chain Fv analogue produced in *Escherichia coli*," Proc. Natl. Acad. Sci. U S A., Aug. 1988, 85:5879-5883.
Ilonen et al., "Patterns of beta-cell autoantibody appearance and genetic associations during the first years of life," Diabetes, 2013, 32(10):3636-3640.
International Preliminary Report on Patentability in International Application No. PCT/US2020/036625, dated Dec. 7, 2021, 5 pages.
International Search Report and Written Opinion in International Application No. PCT/US2020/036625, dated Sep. 17, 2020, 7 pages.

Inzucchi et al., "Management of Hyperglycernia in type 2 diabetes: a patient-centered approach: position statement of the American Diabetes Association (ADA) and the European Association for the Study of Diabetes (EASD)," Diabetes Care, Jun. 2012, 35(6):1364-79.
Ionescu-Tirgoviste et al., "A 3D map of the islet routes throughout the healthy human pancreas," Sci Rep, 2015, 5:14634.
Iwahashi et al., "CDR substitutions of a humanized monoclonal antibody (CC49): contributions of individual CDRs to antigen binding and immunogenicity," Mol. Immunol., 1999, 36:1079-1091.
Jarchum et al., "In vivo cytotoxicity of insulin-specific COB+ Tcells in HLA-A*0201 transgenic NOD mice," Diabetes, 2007, 56(10):2551-2560.
Jefferis et al., "Human immunoglobulin allotypes: possible implications for immunogenicity," Mabs, 2009, 1(4):332-338.
Jermutus et al., "Tailoring in vitro evolution for protein affinity or stability," Proc. Natl. Acad. Sci. USA, Dec. 2000, 98:75-80.
Johne et al., "Epitope mapping and binding kinetics of monoclonal antibodies studied by real time biospecific interaction analysis using surface plasmon resonance," J. Immunol. Methods, Apr. 1993, 160(2):191-198.
Johnson et al., "Anti-tumor activity of CC49-doxorubicin immunoconguates," Anticancer Res. 1995, 15:1387-93.
Kambe et al., "Current understanding of ZIP and ZnT zinc transporters in human health and diseases," Cell Mol Life Sci, 2014, 71:3281-3295.
Kambe et al., "Zinc transporters and their functional integration in mammalian cells," J Biol Chem, 2021, 100320.
Kaufman et al., "Amplification and expression of sequences cotransfected with a modular dihydrofolate reductase complementary dna gene," J Mol. Biol. 1982, 159(4):601-621.
Kawasaki, "ZnT8 and type 1 diabetes," Endocrine Journal, 2012, 59(7):531-537.
Kay et al., "Overexpression of class I major histocompatibility complex accompanies insulitis in the nonobese :liabetic mouse and is prevented by anti-interferon-gamma antibody," Diabetologia, 1991, 34(11):779-785.
Kharroubi et al., "Free fatty acids and cytokines induce pancreatic beta-cell apoptosis by different mechanisms: role of nuclear factor-kappaB and endoplasmic reticulum stress," Endocrinology, 2004, 145(11):5087-5096.
Kim et al., "Antibody Engineering for the Development of Therapeutic Antibodies," Molecules and Cells, 2005, 20(1):17-29.
Kim et al., "In situ quantification of pancreatic beta-cell mass in mice," 2010, J Vis Exp, Jun. 2010, 7(40):1970.
Klingensmith et al., "The presence of GAD and IA-2 antibodies in youth with a type 2 diabetes phenotype: results from the TODAY study," Diabetes Care., 2010, 33:1970-1975.
Kodama et al., "Expression-Based Genome-Wide Association Study Links Vitamin D-Binding Protein With A\utoantigenicity in Type 1 Diabetes," Diabetes, 2016, 65(5):1341-1349.
Lam et al., "A new type of synthetic peptide library for identifying ligand-binding activity," Nature, 1991, 354:82-84.
Lamoyi, "Preparation of F(ab')2 fragments from mouse IgG of various subclasses," Methods in Enzymology, 1989, 121:652-663.
Lau et al, "Conjugation of Doxorubicin to Monoclonal Anti-carcinoembryonic Antigen Antibody via Novel Thiol-directed Cross-linking Reagents," Bioorg-Med-Chem., 1995, 3(10):1299-1304.
Lau et al, "Novel doxorubicin-monoclonal anti-carcinoembryonic antigen antibody immunoconjugate activity in vitro," Bioorg-Med-Chem., 1995, 3(10):1305-12.
Lazar et al., "Engineered antibody Fc variants with enhanced effector function," Proc. Natl. Acad. Sci. USA, 2006, 103(11):4005-4010.
Leahy et al., "Chronic hyperglycemia is associated with impaired glucose influence on insulin secretion. A study in normal rats using chronic in vivo glucose infusions," J Clin Invest, 1986, 77(3):908-915.
Lebl et al., "One-Bead-One-Structure Cornbinatorial Libraries," Biopolymers, 1995, 37:177-198.
Lebowitz et al., "Modem analytical ultracentrifugation in protein science: A tutorial review," Protein Science, 2002, 11:2067-2079.

(56) References Cited

OTHER PUBLICATIONS

Lei et al., "Characterization of the Erwinia carotovora pelB gene and its product pectate lyase," J. Bacteriol., Sep. 1987, 169(9):4379-4383.

Lemaire et al., "Zinc transporters and their role in the pancreatic B-cell," J Diabetes Investig, Jun. 2012, 3(3):202-211.

Lernmark et al., "Islet-cell-surface antibodies in juvenile diabetes mellitus," N Engl J Med, 1978, 299:375-380.

Li et al., "A syntaxin 1, Galpha{o}, and N-type calcium channel complex at a presynaptic nerve terminal: analysis by quantitative immunocolocalization," J Neurosci, 2004, 24(16):4070-4081.

Li et al., "hZnT8 (Slc30a8) Transgenic Mice That Overexpress the R325W Polymorph Have Reduced Islet Zn2+ and Proinsulin Levels, Increased Glucose Tolerance After a High-Fat Diet, and Altered Levels of Pancreatic Zinc Binding Proteins," Diabetes, Feb. 2017, 66(2):551-559.

Li et al., "Identification of novel HLA-A 0201-restricled cytotoxic T lymphocyte epilopes from Zinc Transporter 8," Vaccine, 2013, 31(12):1610-1615.

Li et al., "Temporal Proteomic Analysis of Pancreatic beta-Cells in Response to Lipotoxicity and Glucolipotoxicity," Mol Cell Proteomics, 2018, 17(11):2119-2131.

Lim et al., "High-efficiency screening of monoclonal antibodies for membrane protein crystallography," PLoS One, 2011, 6(9):e24653.

Lippow et al., "Computational design of antibody-affinity improvement beyond in vivo maturation," Nat. Biotechnol., 2005, 25(10):1171-1176.

Liston et al., "Beta-Cell Fragility As a Common Underlying Risk Factor in Type 1 and Type 2 Diabetes," Trends Mol Med, 2017, 23:181-194.

Liu et al., "Characterization of Zinc Influx Transporters (ZIPs) in Pancreatic beta Cells: Roles in Regulating Cytosolic Zinc Homeostasis and Insulin Secretion," J Biol Chem, 2015, 290(30):18757-18769.

Liu et al., "Proinsulin maturation, misfolding, and proteotoxicity," Proc Natl Acad Sci USA, 2007, 104:15841-15846.

Long et al., "Rising incidence of type 1 diabetes is associated with altered immunophenotype at diagnosis," Diabetes, 2012, 61:683-686.

Lu et al., "Structure of the zinc transporter YiiP," Science, 2007, 317(5845):1746-1748.

Lukowiak et al., "Identification and purification of functional human beta-cells by a new specific zinc-fluorescent probe," J Histochem Cytochem, Apr. 2001, 49(4):519-528.

Lund et al., "Human Fc gamma RI and Fc gamma RII interact with distinct but overlapping sites on human IgG," J Immun., Oct. 1991, 147:2657-62.

Madden et al., "Synthetic Combinatorial Libraries: Views on Techniques and Their Application,," Perspectives in Drug Discovery and Design, 1995, 2:269-282.

Maedler et al., "Distinct effects of saturated and monounsaturated fatty acids on betacell turnover and function," Diabetes, 2001, 50(1):69-76.

Mathiowitz et al., "Biologically erodable microssheres as potential oral drug delivery systems," Nature, 1997, 386(6623):410-4.

Mattila et al, "Extensive allelic sequence variation in the J region of the human immunoglobulin heavy chain gene locus," Eur. J. Immunol., 1995, 25:2578-2582.

Meng et al., "Epoxomicin, a potent and selective proteasome inhibitor, exhibits in vivo antiinflammatory activity," Proc Natl Acad Sci USA, 1999, 96(18):10403-10408.

Merriman et al., "A subclass of serum anti-ZnT8 antibodies directed to the surface of live pancreatic beta-cells," J Biol Chem, 2018, 293(2):579-587.

Merriman et al., "Down-regulation of the islet-specific zinc transporter-8 (ZnT8) protects human insulinoma cells against inflammatory stress," J Biol Chem, 2019, 294:16992-17006.

Merriman et al., "Highly specific monoclonal antibodies for allosteric inhibition and immunodetection of the human pancreatic zinc transporter ZnT8," J Biol Chem, 2018, 293(42):16206-16216.

Milenic et al, "Construction, Binding Properties, Metabolism, and Tumor Targeting of a Single-Chain Fv Derived from the Pancarcinoma Monoclonal Antibody CC49," Cancer Research, 1991, 51:6363-6371.

Millstein et al., "Hybrid hybridomas and their use in immunohistochemistry," Nature, Oct. 1983, 305:537-539.

Mittermayer et al., "Addressing unmet medical needs in type 2 diabetes: a narrative review of drugs under :levelopmenl," Curr Diabetes Rev, 2015, 11(1):17-31.

Mizushima et al., "pEF-BOS, a powerful mammalian expression vector," Nucleic Acids Res., 1990, 18:5322.

Morgan et al., "The N-terminal end of the CH2 domain of chimeric human IgG1 anti-HLA-DR is necessary for C1q, Fc gamma RI and Fc gamma RIII binding," Immunology, 1995, 86(5):319-24.

Morton et al., "Kinetic analysis of macromolecular interactions using surface plasmon resonance hiosensors" Methods in Enzymology, 1998, 295:268-294.

Mulligan et al., "Synthesis of rabbit β-globin in cultured monkey kidney cells following infection with a SV40 β-globin recombinant genome," Nature, 1979, 277:108-114.

Murata et al., "The immunoproteasome and thymoproteasome: functions, evolution and human disease," Nat Immunol, 2018, 19(9):923-931.

Muratore et al., "The vascular architecture of the pancreatic islets: A homage to August Krogh," Comp Biochem Physiol A Mol Integr Physiol, 2021, 252:110846.

NCBI Accession No. ABQ59023. 1, "SLC30A8 protein [*Homo sapiens*]".

NCBI Accession No. KR712225. 1, "Synthetic construct *Homo sapiens* clone CCSBHm_00900180 SLC30A8 (SLC30A8) mRNA, encodes complete protein."

Neumann et al., "Gene transfer into mouse lyoma cells by electroporation in high electric fields," EMBO J., 1982, 1(7):841-845.

Neville et al, "Enhancement of Immunotoxin Efficacy by Acid-cleavable Cross-linking Agents Utilizing Diphtheria Toxin and Toxin Mutants," Journal of Biological Chemistry., 1989, 264(25):14653-14661.

Nicolson et al., "Insulin storage and glucose homeostasis in mice null for the granule zinc transporter ZnT8 and studies of the type 2 diabetes-associated variants," Diabetes, 2009, 58(9):2070-2083.

Noguchi et al., "Pharmacokinetic prediction of an antibody in mice based on an in vitro cell-based approach using target receptor-expressing cells," Sci Rep, 2020, 10:16268.

Ohana et al., "Identification of the Zn2+ binding site and mode of operation of a mammalian Zn2+ transporter," J Biol Chem, Jun. 2009, 284(26):17677-86.

Ohashi et al., "Zinc Transporter SLC39A7/ZIP7 Promotes Intestinal Epithelial Self-Renewal by Resolving ER Stress," DLoS Genet, 2016, 12 (10):e1006349.

Ovacik et al., "Tutorial on Monoclonal Antibody Pharmacokinetics and Its Considerations in Early Development," Clin Transl Sci, 2018, 11:540-552.

Pantoliano et al, "Conformational stability, folding, and ligand-binding affinity of single-chain Fv immunoglobulin fragments expressed in *Escherichia coli*," Biochemistry, 1991, 30(42):10117-10125.

Parsons et al., "The C-terminal cytosolic domain of the human zinc transporter ZnT8 and its diabetes risk variant," FEBS J, 2018, 285(7):1237-1250.

PCT International Preliminary Report on Patentability in International Application No. PCT/US2017/029250, dated Oct. 30, 2018, 5 pages.

PCT International Preliminary Report on Patentability in International Application No. PCT/US2019/046747, dated Feb. 16, 2021, 7 pages.

PCT International Search and Written Opinion in International Application No. PCT/US2017/029250, dated Aug. 17, 2017, 6 pages.

PCT International Search Report and Written Opinion in International Application No. PCT/US2019/046747, dated Nov. 28, 2019, 8 pages.

PCT Invitation to Pay Additional Fees And, Where Applicable, Protest Fee in International Application No. PCT/US2022/075156, dated Nov. 3, 2022, 2 pages.

(56) References Cited

OTHER PUBLICATIONS

Pearson, "Zinc transport and diabetes risk," Nat Genet, Apr. 2014, 46(4):323-4.
Peterson et al., "A long-lived IL-2 mutein that selectively activates and expands regulatory T cells as a therapy for autoimmune disease," J Autoimmun, 2018, 95:1-14.
Pettersen et al., "UCSF Chimera-α visualization system for exploratory research and analysis," J Comput Chem, Oct. 2004, 25(13):1605-12.
Pierce et al, "Isothermal Titration Calorimetry of Protein-Protein Interactions," Methods, 1999, 19:213-221.
Pietropaolo et al., "Primer: immunity and autoimmunity," Diabetes, 2008, 57(11):2872-2882.
Pluckthun et al., "Expression of functional antibody Fv and Fab fragments in *Escherichia coli*," Methods in Enzymology, 1989, 178:497-515.
Poitout et al., "Glucolipotoxicity of the pancreatic beta cell," Biochim Biophys Acta, 2010, 1801(3):289-298.
Pound et al., "Deletion of the mouse Slc30a8 gene encoding zinc transporter-8 results in impaired insulin secretion," Biochem J, 2009, 421(3):371-376.
Pound et al., "The physiological effects of deleting the mouse SLC30A8 gene encoding zinc transporter-8 are nfluenced by gender and genetic background," PLoS One, 2012, 7(7):e40972.
Prasad et al., "Genetics of Type 2 Diabetes—Pitfalls and Possibilities," Genes (Basel), Mar. 2015, 6(1):87-123.
Punjani et al., "cryoSPARC: algorithms for rapid unsupervised cryo-EM structure determination," Nat Methods, Mar. 2017, 14(3):290-296.
Qian et al., "Screening and identification of human ZnT8-specific single-chain variable fragment (scFv) from type 1 diabetes phage display library," Science China Life Sciences, Jun. 2016, 59(7):686-693.
Rajpal et al., "A general method for greatly improving the affinity of antibodies by using combinatorial libraries," PNAS, 2005, 102(24):8466-71.
Ravassard et al., "A genetically engineered human pancreatic beta cell line exhibiting glucose-inducible insulin secretion," J Clin Invest, 2011, 121(9):3589-3597.
Regazzi et al., "VAMP-2 and cellubrevin are expressed in pancreatic beta-cells and are essential for Ca(2+)—but not or GTP gamma S-induced insulin secretion," EMBO J, 1995, 14(12):2723-2730.
Robertson et al., "Beta-cell glucose toxicity, lipotoxicity, and chronic oxidative stress in type 2 diabetes," Diabetes, 2004, 53(Suppl 1):S119-124.
Roep et al., "Type 1 diabetes mellitus as a disease of the beta-cell (do not blame the immune system?)," Nat Rev Endocrinol, 2021, 17:150-161.
Rohou et al., "CTFFIND4: Fast and accurate defocus estimation from electron micrographs," J Struct Biol, Nov. 2015, 192(2):216-21.
Rojas et al., "Pancreatic Beta Cell Death: Novel Potential Mechanisms in Diabetes Therapy," J Diabetes Res, 2018, 9601801.
Rousseaux et al., "Optimal conditions for the preparation of proteolytic fragments from monoclonal IgG of different rat IgG subclasses," Methods in Enzymology, 1989, 121:663-669.
Rutter, "Think zinc: New roles for zinc in the control of insulin secretion," Islets, Jan.-Feb. 2010, 2(1):49-50.
Saltiel et al., "Inflammatory mechanisms linking obesity and metabolic disease," J Clin Invest, 2017, 127(1):1-4.
Saunders et al., "Ectonucleoside Triphosphate Diphosphohydrolase-3 Antibody Targets Adult Human Pancreatic beta Cells for In Vitro and In Vivo Analysis," Cell Metab, Mar. 2019, 29(3):745-754.e4.
Scheres, "RELION: implementation of a Bayesian approach to cryo-EM structure determination," J Struct Biol, Dec. 2012, 180(3):519-30.
Scheuner et al., "The unfolded protein response: a pathway that links insulin demand with beta-cell failure and diabetes," Endocr Rev, 2008, 29(3):317-333.
Schuit et al., "Glucose stimulates proinsulin biosynthesis by a dose-dependent recruitment of pancreatic beta cells," Droc Natl Acad Sci USA, 1988, 85(11):3865-386.
Schwanhausser et al., "Global quantification of mammalian gene expression control," Nature, 2011, 473:337-342.
Scott et al., "A genome-wide association study of type 2 diabetes in Finns detects multiple susceptibility variants," Science, Jun. 2007, 316(5829):1341-5.
Scotto et al., "Zinc transporter {ZnT)8{186-194) is an immunodominant COB+ T cell epitope in HLA-A2+ type 1 dliabetic patients," Diabetologia, 2012, 55(7):2026-2031.
Segerstolpe et al., "Single-Cell Transcriptome Profiling of Human Pancreatic Islets in Health and Type 2 Diabetes," Cell Metab, 2016, 24(4):593-607.
Shields et al, "High resolution mapping of the binding site on human IgG1 for Fc gamma RI, Fc gamma RII, Fc gamma RIII, and FcRn and design of IgG1 variants with improved binding to the Fc gamma R, High resolution mapping of the binding site on human IgG1 for Fc gamma RI, Fc gamma RII, Fc gamma RIII, and FcRn and design of IgG1 variants with improved binding to the Fc gamma R," J. Biol. Chem., 2001, 276(9):6591-604.
Shin et al, "Physical map of the 3' region of the human immunoglobulin heavy chain locus: clustering of autoantibody-related variable segments in one haplotype," EMBO J. 1991, 10:3641-3645.
Sjolander et al., "Integrated fluid handling system for biomolecular interaction analysis," Anal. Chem, 1991, 63:2338-2345.
Skarstrand et al., "Zinc transporter 8 (ZnT8) autoantibody epitope specificity and affinity examined with ecombinant ZnT8 variant proteins in specific ZnT8R and ZnT8W autoantibody-positive type 1 diabetes patients," Clinical & Experimental Immunology, 2015, 179(2):220-229.
Sladek et al., "A genome wide association study identifies novel risk loci for ty5e 2 diabetes," Nature, 2007, 445:881-885.
Soja et al., "A chemical method for the deglycosylation of proteins," Arch. Biochem. Biophys., 1987, 259(1):52-57.
Solimena et al., "ICA 512, an autoantigen of type I diabetes, is an intrinsic membrane protein of neurosecretory granules," EMBO J, 1996, 15(9):2102-2114.
Steck et al., "Predictors of Progression From the Appearance of Islet Autoantibodies to Early Childhood Diabetes: The Environmental Determinants of Diabetes in the Young (TEDDY)," Diabetes Care., 2015, 38(5):808-813.
Stull et al., "Mouse islet of Langerhans isolation using a combination of purified collagenase and neutral protease," J Vis Exp., Sep. 2012, 67:4137.
Stumvoll et al., "Type 2 diabetes: principles of pathogenesis and therapy," Lancet, Apr. 9-15, 2005, 365(9467):1333-46.
Sun et al., "Gene silencing of ZnT8 attenuates inflammation and protects pancreatic tissue injury in T1D," Immunology Letters, Jun. 2018, 198:1-6.
Surface Plasmons on Smooth and Rough Surfaces and on Gratings, Springer Verlag, 1988, 140 pages.
Szabo et al., "Surface plasmon resonance and its use in biomolecular interaction analysis (BIA)," Curr. Opin. Struct. Biol. Oct. 1995, 5(5):699-705.
Szoka et al., "Comparative properties and methods of preparation of lipid vesicles (liposomes)," Annu Rev Biophys Bioeng, 1980, 9:467-508 9.
Takenaga et al., "Microparticle resins as a potential nasal drug delivery system for insulin," J Control Release, 1998, 52:81-87.
Takkinen et al, "An active single-chain antibody containing a cellulase linker domain is secreted by *Escherichia coli*," Protein Engineering, 1991, 4:837-841.
Tamaki et al., "The diabetes-susceptible gene SLC30A8/ZnT8 regulates hepatic insulin clearance," J Clin Invest, Oct. 2013, 123(10):4513-24.
Tamura et al., "Structural Correlates of an Anticarcinoma Antibody: Identification of Specificity-Determining Residues (SDRs) and Development of a Minimally Immunogenic Antibody Variant by Retention of SDRs Only," Journal of Immunology, 2000, 164(3):1432-1441.

(56) References Cited

OTHER PUBLICATIONS

Taylor et al., "Protein kinase CK2 triggers cytosolic zinc signaling pathways by phosphorylation of zinc channel ZIP7," Sci Signal, 2012, 5(210):ra11.
Thomas et al., "The natural autoantibody repertoire of nonobese diabetic mice is highly active," J Immunol, 2002, 169(11):6617-6624.
Thorpe et al., "New Coupling Agents for the Synthesis of Immunotoxins Containing a Hindered Disulfide Bond with Improved Stability in Vivo," Cancer Res., 1987, 47(22):5924-5931.
Thorpe et al., "The preparation and cytotoxic properties of antibody-toxin conjugates," Immunol. Rev., 1982, 62:119-58.
Thorp-Greenwood et al., "Multimodal radio-(PET/SPECT) and fluorescence imaging agents based on metallo-radioisotopes: current applications and prospects for development of new agents," Dalton Trans, 2011, 40(23):6129-6143.
Thotakura et al., "Enzymatic deglycosylation of glycoproteins," Meth. Enzymol., 1987, 138:350-359.
Thul et al., "A subcellular map of the human proteome," Science, 2017, 356(6340):eaal3321.
Tozzoli, "Receptor autoimmunity: diagnostic and therapeutic implications," Auto Immun Highlights, 2020, 11:1.
Tsai et al., "Are obesity-related insulin resistance and type 2 diabetes autoimmune diseases?" Diabetes, 2015, 64(6):1886-1897.
Tuncay et al., "Hyperglycemia-Induced Changes in ZIP7 and ZnT7 Expression Cause $Zn\{2+\}$ Release From the Sarco(endo)plasmic Reticulum and Mediate ER Stress in the Heart," Diabetes, 2017,66(5):1346-1358.
Urlaub et al., "Isolation of Chinese hamster cell mutants deficient in dihydrofolate reductase activity," Proc. Natl. Acad. Sci. USA, 1980, 77:4216-4220.
Ustinova et al., "Characterization of monoclonal ZnT8-specific antibody," Frontiers in Immunology, Jan. 2013, retrieved from URL<https://internal-www.frontiersin.org/Community/AbstractDetails.aspx?ABS_DOI=10.3389/conf.fimmu.2013.02.00326&eid=&sname=>, 2 pages.
Vajdos et al., "Comprehensive functional maps of the antigen-binding site of an anti-ErbB2 antibody obtained with shotgun scanning mutagenesis," Journal of Molecular Biology, Jul. 2002, 320(2): 415-428.
Vinkenborg et al., "Genetically encoded FRET sensors to monitor intracellular Zn2+ homeostasis," Nat Methods, 2009, 6(10):737-740.
Vyas et al., "Molecular recognition of oligosaccharide epitopes by a monoclonal Fab specific for Shigella flexneri Y ipopolysaccharide: X-ray structures and thermodynamics," Biochemistry, Nov. 19, 2002, 41(46):13575-86.
Wan et al., Proteoliposome-based full-length Zn TB self-antigen for type 1 diabetes diagnosis on a plasmonic platform, Proc Natl Acad Sci USA, 2017, 114(38):10196-10201.
Ward et al., "Binding activities of a repertoire of single immunoglobulin variable domains secreted from *Escherichia coli*," Nature, Oct. 1989, 341:544-546.
Wenzlau et al., "Changes in Zinc Transporter 8 Autoantibodies Following Type 1 Diabetes Onset: The Type 1 Diabetes Genetics Consortium Autoantibody Workshop," Diabetes Care, 2015, 38(Supplement 2):S14-20.
Wigler et al., "Biochemical transfer of single-copy eucaryotic genes using total cellular DNA as donor," Cell, 1978, 14(3):725-731.
Wijesekara et al., "Beta cell-specific Znt8 deletion in mice causes marked defects in insulin processing, crystallisation and secretion," Diabetologia, 2010, 53(8):1656-1668.
Winkel et al., "Islet cell surface antibodies from insulin-dependent diabetics bind specifically to pancreatic B cells," J Clin Invest, 1982, 70(1):41-49.
Wong et al., "Exploring the Association Between Demographics, SLC30A8 Genotype, and Human Islet Content of Zinc, Cadmium, Copper, Iron, Manganese and Nickel," Sci Rep, 2017, 7(1):473.
Woodruff et al., "The Zinc Transporter SLC39A7 (ZIP7) Is Essential for Regulation of Cytosolic Zinc Levels," Mol Dharmacol, 2018, 94(3):1092-1100.
Wu et al., "An electrochemiluminescence (ECL)-based assay for the specific detection of anti-drug antibodies of the IgE isotype," J Pham Biomed Anal, 2013, 86:73-81.
Xue et al., "Cryo-EM structures of human ZnT8 in both outward- and inward-facing conformations," Elife, 2020, 9:e58823.
Yi et al., "Different role of zinc transporter 8 between type 1 diabetes mellitus and type 2 diabetes mellitus" J Diabetes Investig, 2016, 7:459-465.
Yu et al., "Antiislet autoantibodies usually develop sequentially rather than simultaneously," Journal of Clinical Endocrinology & Metabolism, 1996, 81(12):4264-4267.
Yu et al., "Early expression of antiinsulin autoantibodies of humans and the NOD mouse: evidence for early dletermination of subsequent diabetes," Proc Nall Acad Sci USA, 2000, 97(4):1701-1706.
Yu et al., "Identification of Candidate Tolerogenic CD8(+) T Cell Epitopes for Therapy of Type 1 Diabetes in the NOD Mouse Model," J Diabetes Res, 2016, 2016:9083103.
Yu et al., "Proinsulin/Insulin autoantibodies measured with electrochemiluminescent assay are the earliest indicator of prediabetic islet autoimmunity," Diabetes Care, 2013, 36(8):2266-2270.
Zeggini et al., "Replication of genome-wide association signals in UK samples reveals risk loci for type 2 diabetes," Science, Jun. 1, 2007, 316(5829):1336-41.
Zhang et al., "A Simple Statistical Parameter for Use in Evaluation and Validation of High Throughput Screening Assays," J Biomol Screen, 1999, 4(2):67-73.
Ziegler et al., "Seroconversion to multiple islet autoantibodies and risk of progression to diabetes in children," JAMA, 2013, 309(23):2473-2479.
Zumsteg et al., "Nitric oxide production and Fas surface expression mediate two independent pathways of cytokinenduced murine beta-cell damage," Diabetes, 2000, 49(1):39-47.
Extended European Search Report in European Application No. 18832105.3, dated Mar. 11, 2021, 11 pages.
International Preliminary Report on Patentability in International Appln. No. PCT/US2018/040890, dated Jan. 14, 2020, 6 pages.
International Search Report and Written Opinion in International Appln. No. PCT/US2018/040890, dated Oct. 25, 2018, 8 pages.
International Search Report and Written Opinion in International Appln. No. PCT/US2022/075156, dated Jan. 10, 2023, 13 pages.
Koh et al., "Visible to Near-Infrared Fluorescence Enhanced Cellular Imaging on Plasmonic Gold Chips," small, Jan. 27, 2016, 12(4):457-465 (abstract only).
European Search Report in European Application No. 20817829.3, dated Jun. 1, 2023, 20 pages.
GenBank Accession No. NM_001172814.1, "*Homo sapiens* solute carrier family 30 (zinc transporter), member 8 (SLC30A8), transcript variant 2, mRNA," dated Mar. 15, 2015, 5 pages.
Gu et al., "Identification of Autoantibodies to ZnT8 Extracellular Epitope(s) in Patients with TID," Diabetes, 79th Scientific Sessions of the American-Diabetes-Association (ADA), Jun. 7-11, 2019, 68(Suppl. 1):162-OR.
Hwang et al., "Budding yeast Cdc20: a target of the spindle checkpoint," Science, Feb. 1998, 279(5353):1041-1044 (abstract only).

* cited by examiner

PROTEOLIPOSOME-BASED ZNT8 SELF-ANTIGEN FOR TYPE 1 DIABETES DIAGNOSIS

CROSS-REFERENCE TO RELATED APPLICATIONS

This application is a 35 U.S.C. § 371 U.S. national entry of International Application PCT/US2018/040890, having an international filing date of Jul. 5, 2018, which claims the benefit of U.S. Provisional Application No. 62/531,525, filed Jul. 12, 2017, the content of each of the aforementioned applications is herein incorporated by reference in their entirety.

STATEMENT OF GOVERNMENTAL INTEREST

This invention was made with government support under grant no. R01GM065137 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jun. 27, 2018, is named P14838-02_SL.txt and is 12,449 bytes in size.

BACKGROUND OF THE INVENTION

The incidence of type 1 diabetes (T1D) in children has been increasing by 3% to 5% per year worldwide since the 1960s, which makes the sensitive and specific T1D diagnosis imperative. Detection of T1D-related autoantibodies can quantify the extent of risk for symptomatic T1D onset, as well as afford enrollment into trails seeking to prevent overt disease development. Unlike the earlier established autoantibodies against insulin, islet antigen 2 (IA2), and glutamic acid decarboxylase (GAD) as three major biomarkers for T1D diagnosis, zinc transporter 8 autoantibody (ZnT8A) was discovered more recently as another major biomarker for T1D diagnosis through bioinformatics, expanding the panel of T1D diagnostic autoantibodies. In pre-diabetic individuals, ZnT8A appears in the prodromal phase months to years prior to the clinical onset of disease and its detection can improve the accuracy of T1D prediction, rendering ZnT8A as one of the most important biomarkers to evaluate the risk of T1D development.

ZnT8 is a specialized zinc transporter found predominantly in insulin secretory granules of pancreatic beta-cells[4]. It is a multi-spanning transmembrane protein consisting of two functional modules, a transmembrane domain responsible for zinc transport and a cytosolic zinc-sensing unit of N- and C-terminal domains (NTD and CTD, respectively). The transport activity of ZnT8 yields a highly enriched granular zinc content for crystalline packaging of insulin molecules in complex with zinc ions. During insulin secretion, granule exocytosis exposes ZnT8 to the surface membrane, subjecting its transmembrane domain to extracellular ZnT8A surveillance. The cytosolic domains of ZnT8 only become accessible to ZnT8A following the destruction of beta-cells. Approximately half of the ZnT8 structure lies within six membrane-spanning regions, presenting a challenge to develop assays for ZnT8A detection due to the difficulty of maintaining its tertiary structure outside a membrane environment.

Thus far, most assays for ZnT8A detection are based on antigens of cytosolic domains of ZnT8 (i.e., CTD and NTD) or construction of single-chain molecules fusing the two domains. Due to the fact that CTD encompassing amino acid (aa) 275-369 can produce a robust detection performance relative to the less efficient detection performance based on NTD, ZnT8A detection has focused on two variants of CTD that differ by a single aa at position 325 (i.e., arginine, 325R or tryptophan, 325W). Although thus far the combination of the two variants of CTD has been used for effective ZnT8A detection, the best candidate for ZnT8A detection could be full-length ZnT8 that contains the complete auto-reactive sites (both intracellular and extracellular ones) accessible to ZnT8A. However due to the instability of purified full-length ZnT8 protein in its detergent-solubilized form, full-length ZnT8 has thus far not been used successfully for ZnT8A detection.

Other researchers have tried to incorporate a full-length ZnT8 protein into synthetic nano-discs containing phospholipid and apolipoproteins (Janet M. Wenzlau and John C. Hutton, Curr Diab Rep. 2013 October; 13(5): doi: 10.1007/s 1892-013-0405-9). A nanodisc is a synthetic model membrane system that assists in the study of membrane proteins. It is composed of a lipid bilayer of phospholipids with the hydrophobic edge screened by two amphipathic proteins. These proteins are called membrane scaffolding proteins (MSP) and align in double belt formation. Nanodiscs are structurally very similar to high-density lipoproteins (HDL) and the MSPs are modified versions of apolipoprotein A1 (apoA1), the main constituent in HDL. Nanodiscs are useful in the study of membrane proteins because they can solubilize and stabilize membrane proteins and represent a more native environment than liposomes, detergent micelles, bicelles and amphipols.

SUMMARY OF THE INVENTION

One embodiment of the present invention is a method of detecting ZNT8 antibodies in serum comprising: forming a mixture by combining proteoliposomes having an interior and an exterior comprising protein sequences of a transmembrane domain (TMD) and a cytosolic domain (CTD) of ZnT8 proteins exposed on the exterior of the proteoliposomes; serum comprising antibodies targeting the protein sequences; a labelled secondary antibody that binds to the antibodies targeting the protein sequences; and measuring the amount of antibodies bound to the protein sequences. The transmembrane domain and the cytosolic domain may be from the same ZnT8 protein or from different full length ZnT8 proteins.

Another embodiment of the present invention is a method of detecting ZNT8 antibodies in serum comprising the following steps. Providing a collection of proteoliposomes having an interior and an exterior wherein some proteoliposomes have protein sequences of a transmembrane domain (TMD) of a ZnT8 on its exterior and other proteoliposomes comprise protein sequences of a cytosolic domain (CTD) of a ZnT8 protein exposed on its exterior. Adding serum comprising antibodies targeting the protein sequences of TMD and/or CTD forming proteoliposomes bound to the antibodies. Adding a labelled secondary antibody that binds to the antibodies bound to the proteoliposomes and measuring the amount of antibodies targeting the protein sequences of TMD and/or CTD bound to the proteoliposomes.

Suitable protein sequences of a TMD and a CTD used in the present invention may be full length TMD and CTD domains part of a full length ZnT8 protein, for example. Other suitable sequences include parts (or fragments) of TMD or CTD that are antigenic and bind to the antibodies targeting TMS and/or CTD. Suitable ZnT8 proteins used in the present invention include a wild type human ZnT8 protein and variants thereof. Examples of variants include an "a" form of a ZnT8 protein including a signal sequence, and a "b" form of a ZnT8 protein without a signal sequence. Please see the Methods Section for examples of ZnT8 protein sequences used in the present invention. In addition, both the "a" form and the "b" form of ZnT8 may be a R325W variant.

A collection of proteoliposomes used in the present invention may comprises "inside out" proteoliposomes and "right side out" proteoliposomes. The "inside out" proteoliposomes preferably comprise CTD protein sequences on its exterior. The "right side" out proteoliposomes preferably comprise TMD protein sequences on its exterior.

The proteoliposomes used in the methods of the present invention may be placed on a chip. Please see FIG. 1B and FIG. 5. It is suitable for the mixture to be placed, or printed, on a platform such as a plate or a chip, as examples, wherein the ZnT8 proteins are bound to the plate or chip. An example of a suitable chip includes a pGOLD chip. Secondary proteins are bound to the platform selected from the group comprising: IA2, GADA, and a combination thereof. Any animal serum may be used in the present invention such as human serum. If human serum is used in the present invention, then it is preferred that human ZnT8 proteins be used to form the mixture described above. It is suitable for serum, such as human serum to be diluted with fetal bovine serum (FBS) in the range of 10 to 30 fold with the fetal bovine serum (FBS). The labelled secondary antibody used in the present invention may comprise a detection probe such as a biotin probe or a fluorescent probe, as examples. It is suitable for the measuring step of the present invention to quantify the amount of antibodies bound to the ZnT8 proteins. The amount of antibodies bound to the ZnT8 proteins maybe determined by measuring the signal provided by the detection probe. For example, fluorescence intensity may be analyzed if the labelled secondary antibodies comprise a fluorescent label and by using an infrared scanner to measure the fluorescent signal, as an example. Suitable proteoliposomes used in the present invention may comprise lipids such as 1,2-dioleoyl-sn-glycero-3-phophocholine; 1,2-dioleoyl-sn-glycero-3-phospho-(1'-rac-glycerol); 1,2-dioleoyl-sn-glycero-3-phoethaolamine; or a combination thereof, as examples. Suitable antibodies targeting the ZnT8 proteins used in the present invention include ZnT8 antibodies directed to the transmembrane domain (TMD) of ZnT8, the cytosolic C-terminal domain (CTD) of ZnT8, or a combination thereof. It is preferred that a population of ZnT8 antibodies including ZnT8 antibodies directed to the transmembrane domain (TMD) and ZnT8 antibodies directed to the cytosolic C-terminal domain (CTD) be used in the present invention. The methods of the present invention have a detection performance of greater than 70% sensitivity and greater than 90% specificity.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

The term "activity" refers to the ability of a gene to perform its function such as Indoleamine 2,3-dioxygenase (an oxidoreductase) catalyzing the degradation of the essential amino acid tryptophan (trp) to N-formyl-kynurenine.

The term "antibody," as used in this disclosure, refers to an immunoglobulin or a fragment or a derivative thereof, and encompasses any polypeptide comprising an antigen-binding site, regardless of whether it is produced in vitro or in vivo. The term includes, but is not limited to, polyclonal, monoclonal, monospecific, polyspecific, non-specific, humanized, single-chain, chimeric, synthetic, recombinant, hybrid, mutated, and grafted antibodies. Unless otherwise modified by the term "intact," as in "intact antibodies," for the purposes of this disclosure, the term "antibody" also includes antibody fragments such as Fab, F(ab')$_2$, Fv, scFv, Fd, dAb, and other antibody fragments that retain antigen-binding function, i.e., the ability to bind, for example, PD-L1, specifically. Typically, such fragments would comprise an antigen-binding domain.

The terms "antigen-binding domain," "antigen-binding fragment," and "binding fragment" refer to a part of an antibody molecule that comprises amino acids responsible for the specific binding between the antibody and the antigen. In instances, where an antigen is large, the antigen-binding domain may only bind to a part of the antigen. A portion of the antigen molecule that is responsible for specific interactions with the antigen-binding domain is referred to as "epitope" or "antigenic determinant." An antigen-binding domain typically comprises an antibody light chain variable region ($V_L$) and an antibody heavy chain variable region ($V_H$), however, it does not necessarily have to comprise both. For example, a so-called Fd antibody fragment consists only of a $V_H$ domain, but still retains some antigen-binding function of the intact antibody.

Binding fragments of an antibody are produced by recombinant DNA techniques, or by enzymatic or chemical cleavage of intact antibodies. Binding fragments include Fab, Fab', F(ab')2, Fv, and single-chain antibodies. An antibody other than a "bispecific" or "bifunctional" antibody is understood to have each of its binding sites identical. Digestion of antibodies with the enzyme, papain, results in two identical antigen-binding fragments, known also as "Fab" fragments, and a "Fc" fragment, having no antigen-binding activity but having the ability to crystallize. Digestion of antibodies with the enzyme, pepsin, results in a F(ab')2 fragment in which the two arms of the antibody molecule remain linked and comprise two-antigen binding sites. The F(ab')2 fragment has the ability to crosslink antigen. "Fv" when used herein refers to the minimum fragment of an antibody that retains both antigen-recognition and antigen-binding sites. "Fab" when used herein refers to a fragment of an antibody that comprises the constant domain of the light chain and the CHI domain of the heavy chain.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

By "Diagnostic" means identifying the presence or nature of a pathologic condition, i.e., type 1 diabetes. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

By "disease" is meant any condition or disorder that damages or interferes with the normal function of a cell, tissue, or organ. Examples of diseases include cancer.

By "DS-ZnT8" is meant purified full-length ZnT8 protein in detergent micelles.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "express" is meant the ability of a gene to express the gene product including for example its corresponding mRNA or protein sequence (s).

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "hybridization" is meant hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "immunoassay" is meant an assay that uses an antibody to specifically bind an antigen (e.g., a marker). The immunoassay is characterized by the use of specific binding properties of a particular antibody to isolate, target, and/or quantify the antigen.

By "liposome" is meant an aqueous compartment enclosed by a bimolecular phospholipid membrane; a lipid vesicle. A proteoliposome is a liposome into which one or more proteins have been inserted, usually by artificial means.

By "obtaining" as in "obtaining an agent" is meant synthesizing, purchasing, or otherwise acquiring the agent.

By "mAb" is meant a monoclonal antibody. Antibodies of the invention comprise without limitation whole native antibodies, bispecific antibodies; chimeric antibodies; Fab, Fab', single chain V region fragments (scFv), fusion polypeptides, and unconventional antibodies.

By "marker" is meant any protein or polynucleotide having an alteration in expression level or activity that is associated with a disease or disorder. The term "biomarker" is used interchangeably with the term "marker."

By "measuring" is meant methods which include detecting the presence or absence of marker(s) in the sample, quantifying the amount of marker(s) in the sample, and/or qualifying the type of biomarker. Measuring can be accomplished by methods known in the art and those further described herein, including but not limited to immunoassay. Any suitable methods can be used to detect and measure one or more of the markers described herein. These methods include, without limitation, ELISA and bead-based immunoassays (e.g., monoplexed or multiplexed bead-based immunoassays, magnetic bead-based immunoassays).

By "PLR-ZnT8" is meant purified full length ZnT8 protein in proteoliposomes.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

By "reduces" is meant a negative alteration of at least 10%, 25%, 50%, 75%, or 100%.

A "reference" refers to a standard or control conditions such as a sample (human cells) or a subject that is a free, or substantially free, of an agent such as one or more inhibitors of IDO1 and/or a vaccine.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or there between.

As used herein, the term "sensitivity" is the percentage of subjects with a particular disease.

As used herein, the term "specificity" is the percentage of subjects correctly identified as having a particular disease i.e., normal or healthy subjects. For example, the specificity is calculated as the number of subjects with a particular disease as compared to non-cancer subjects (e.g., normal healthy subjects).

By "specifically binds" is meant a compound or antibody that recognizes and binds a polypeptide of the invention, but which does not substantially recognize and bind other molecules in a sample, for example, a biological sample, which naturally includes a polypeptide of the invention.

As used herein, the term "subject" is intended to refer to any individual or patient to which the method described herein is performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100.mu·g/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/ PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

The term "ZnT8" is intended to refer to the (SLC30A8) gene and variants as well as products including nucleic acid and protein sequences derived therefrom. ZnT8 includes modified nucleic acid and amino acid sequences including tags for visualization for example. Examples of ZnT8 nucleic acid and protein sequences suitable for the present invention include: *Homo sapiens* clone SLC30A8 DNA sequence having a NCBI Accession Number KR712225.1 and *Homo sapiens* SLC30A8 protein sequence having a NCBI Accession Number ABQ59023.1 as examples. An example of a ZnT8 gene sequence is SLC30A8 solute carrier family 30 member 8 [*Homo sapiens* (human)] having an NCBI Gene ID: 169026. The ZnT8 used in the present invention may be eukaryotic including human and animal or prokaryotic including bacterial ZnT8 transporters.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

Such treatment (surgery and/or chemotherapy) will be suitably administered to subjects, particularly humans, suffering from, having, susceptible to, or at risk for pancreatic cancer or disease, disorder, or symptom thereof. Determination of those subjects "at risk" can be made by any objective or subjective determination by a diagnostic test or opinion of a subject or health care provider (e.g., genetic test, enzyme or protein marker, a marker (as defined herein), family history, and the like).

DETAILED DESCRIPTION OF THE INVENTION

Figure 1A:
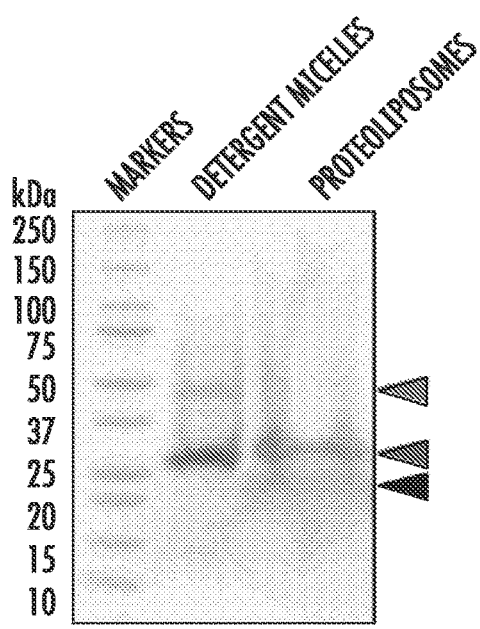
FIG. 1A-1D illustrates the preparation of high-quality full-length ZnT8 antigens. (A) Purified full-length ZnT8 in detergent micelles (DS-ZnT8) or proteoliposomes (PLR-ZnT8) shown by Coomassie blue staining of a SDS-PAGE gel. Magenta, red and dark-brown arrows indicate full-length ZnT8 dimer, monomer and lipids, respectively. (B) A schematic of transmembrane orientations of full-length ZnT8 in reconstituted proteoliposomes as marked. Double layer circles, cyan ribbons, magenta spheres, and green or blue autoantibody represent liposomes, full-length ZnT8, zinc ions, and ZnT8A binding to the extracellular or intracellular surface of full-length ZnT8, respectively. (C) Size-exclusion HPLC profiles of PLR-ZnT8 before (red) and after (blue) vacuum drying (left) and size-exclusion HPLC profiles of DS-ZnT8 before (red) and after (blue) vacuum drying (right). Magenta and black arrows indicate full-length ZnT8 and lipids, respectively. (D) DLS analysis of ZnT8-free liposomes and PLR-ZnT8. The size of liposomes increased from ~104 to ~146 nm after reconstitution of full-length ZnT8.

The present invention is a method of detecting ZnT8 antibodies in a serum. The steps include making a mixture of proteoliposomes preferably comprising a transmembrane domain (TMD) and a cytosolic domain (CTD) of a full length ZnT8 protein on their exterior surfaces. Specifically, the methods of the present invention produce a mixture of proteoliposomes having two distinct transmembrane orientations. The "inside out" proteoliposomes place CTD sequences of full-length ZnT8 on its exterior surface. The "right side out" proteoliposomes exposed TMD sequences on its exterior surface so when this mixture of proteoliposomes are mixed with a serum antibodies targeting TMD and the CTD sequences they are able to bind to these sequences. A labelled secondary antibody then binds to the antibodies present in the serum bound to the TMD and the CTD sequences on the "inside out" and "right side out" proteoliposomes. Finally, the amount of antibody binding to the CTD and the TMD protein sequences are measured.

It is very difficult to express CTD protein sequences on the exterior of proteoliposomes. Surprisingly the inventors were able to identify a method of producing both "inside out" and "right side out" proteoliposomes comprising a full length ZnT8, as an example. A ZnT8 protein is more antigenic in a liposome prepared by the methods of the present invention for the following reasons. Purification of multi-spanning full-length ZnT8 by conventional methods requires detergent solubilization resulting in the lack of structural stability of ZnT8 posing a major challenge to maintaining the proper folding of conformational epitopes. The harsh antigen handling procedures of conventional methods (e.g., drying, rehydration) further exacerbated the loss of bio-activity of full length ZnT8. To overcome these limitations, the inventors developed a proteoliposome-based approach that can dramatically improve the structural stability and proper folding of full-length ZnT8 in a protective lipid matrix, rendering auto-reactive sites accessible to ZnT8 with high bio-activity.

As uncovered to be a major biomarker for type 1 diabetes (T1D) diagnosis, zinc transporter 8 autoantibody (ZnT8A) has shown promise for staging disease risk and disease diagnosis. However, existing assays for ZnT8 autoantibody (ZnT8A) are limited to detection by soluble domains of ZnT8 due to difficulties in maintaining proper folding of a full-length ZnT8 protein outside its native membrane environment. The present invention, through a combination of bioengineering and nanotechnology, was developed using a novel proteoliposome-based full-length ZnT8 self-antigen (full-length ZnT8 proteoliposomes, PLR-ZnT8) for efficient ZnT8A detection on a plasmonic gold chip (pGOLD). The protective lipid matrix of proteoliposomes of the present invention improved the proper folding and structural stability of full-length ZnT8, facilitating PLR-ZnT8 immobilized on pGOLD (PLR-ZnT8/pGOLD) to achieve high-affinity capture of ZnT8A from T1D sera. PLR-ZnT8/pGOLD of the present invention resulted in efficient ZnT8A detection for T1D diagnosis with ~76% sensitivity and ~97% specificity (n=307), superior to assays based on detergent-solubilized full-length ZnT8 (DS-ZnT8) and C-terminal domain of ZnT8 (CTD). Multiplexed assays using pGOLD were also developed for simultaneous detection of ZnT8A, islet antigen 2 autoantibody (IA2A), and glutamic acid decarboxylase autoantibody (GADA) for T1D diagnosis by assessing the three kinds of autoantibodies combined.

The inventors have showed that a single variant of full-length ZnT8 (i.e., 325R) can be used for highly sensitive and specific ZnT8A detection on a gold plasmonic chip. Through expression in human embryonic kidney cells 293 (HEK293), purification of the monodispersed full-length ZnT8 protein and subsequent reconstitution within liposomes, a complex (~146 nm) of full-length ZnT8 proteoliposomes (PLR-ZnT8) with high bio-activity was obtained at a high purity >95%. When immobilized on pGOLD, liposomes can maintain the proper folding of full-length ZnT8, rendering autoreactive sites accessible to ZnT8A. Owing to the novel PLR-ZnT8 and a near-infrared (NIR) fluorescence-enhanced pGOLD platform[8-13], the inventors achieved excellent assay performance of ZnT8A detection with ~76% sensitivity and ~97% specificity for T1D diagnosis using 307 human sera from 138 T1D patients and 169 healthy individuals. The result was superior to the performance of assays based on other ZnT8-related antigens (~2% sensitivity/~94% specificity and ~59% sensitivity/~94% specificity based on DS-ZnT8 and CTD, respectively). Further, the pGOLD-based microarray also demonstrated the potential of multiplexed detection of ZnT8A, IA2A and GADA for future T1D diagnosis.

Preparation of High-Quality Proteoliposomes PLR-ZnT8

Figure 1B:
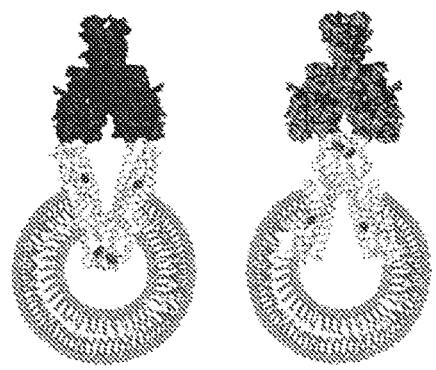
Figure 1C:
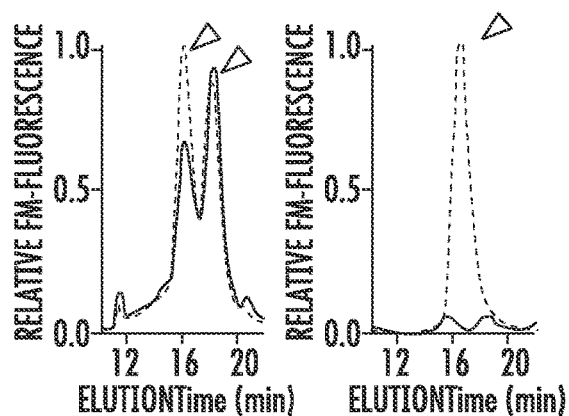
Figure 1D:
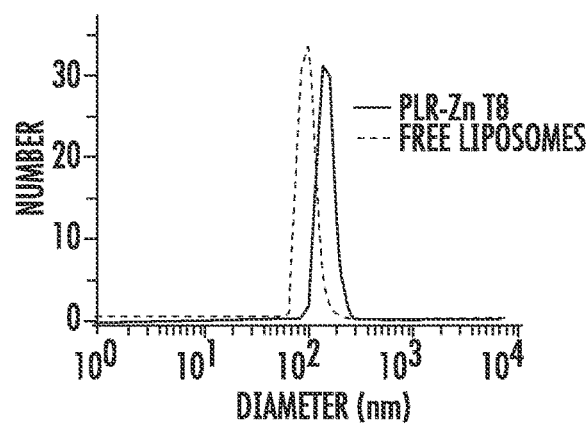

Human ZnT8 is encoded by the SLC30A8 gene expressed in pancreatic beta-cells to produce two protein isoforms. Isoform-1 is a full-length 369-aa protein while isoform-2 is a product of alternative splicing with a 49 aa deletion from the N-terminus. The N-terminal domain of ZnT8 is largely missing in isoform-2. A major arginine variation at position 325 (325R) of human ZnT8 is an immunoreactivity determinant for ZnT8A. The inventors over-expressed the human 325R variant of isoform-2 in HEK293 cells, and purified the recombinant full-length ZnT8 in detergent micelles (DS-ZnT8) or proteoliposomes (PLR-ZnT8, FIG. 1A, see Methods for detailed experimental procedures). DS-ZnT8 was stable in the aqueous solution only for a few hours before forming insoluble protein aggregates accompanied by an irreversible loss of zinc transport activity. PLR-ZnT8, on the other hand, remained functionally active for days on ice and could be stored indefinitely in liquid nitrogen. Re-solubilization of PLR-ZnT8 with detergents yielded well-folded DS-ZnT8, which was subjected to rapid denaturation as indicated by a progressive loss of the initial monodispersed protein population on size-exclusion high-performance-liquid-chromatography (HPLC). The proteoliposomes adopted two different transmembrane orientations (FIG. 1B). The inside-out proteoliposomes mimicked the insulin granules where the cytosolic domains of full-length ZnT8 were exposed to ZnT8A binding. The right-side-out proteoliposomes exposed the transmembrane domain to ZnT8A binding in the same manner as the antigenic presentation of surface-displayed ZnT8 on live beta-cells[16]. Differing from DS-ZnT8 in the aqueous solution, PLR-ZnT8 was a solid-phase antigen that could be separated from the aqueous phase by ultracentrifugation and stored as a lipid-like pellet. Analytical size-exclusion HPLC analysis of detergent extracts of solid PLR-ZnT8 pellets revealed a major monodispersed full-length ZnT8 specie followed by a lipid peak, indicating well-preserved structural integrity of full-length ZnT8 in a wet lipid matrix (FIG. 1C). To further examine the structural integrity of full-length ZnT8 in a completely dried lipid matrix, we vacuum-dried PLR-ZnT8, and then rehydrated the proteoliposomes to mimic experimental conditions of subsequent pGOLD microarray-based assay. HPLC analysis showed that a large majority of full-length ZnT8 remained intact after being dried and rehydration (FIG. 1C). In sharp contrast, DS-ZnT8 was short-lived, losing the monodispersed HPLC profile (FIG. 1C). These results indicated that the lipid matrix of proteoliposomes enhanced the bio-stability of the reconstituted full-length ZnT8. According to dynamic light scattering analysis (DLS), the size of ZnT8-free liposomes centered on ~104 nm with a narrow distribution and increased to ~146 nm after reconstitution of full-length ZnT8 (FIG. 1D).

PLR-ZnT8 Immobilized on pGOLD for Efficient ZnT8A Detection

Figure 2A:
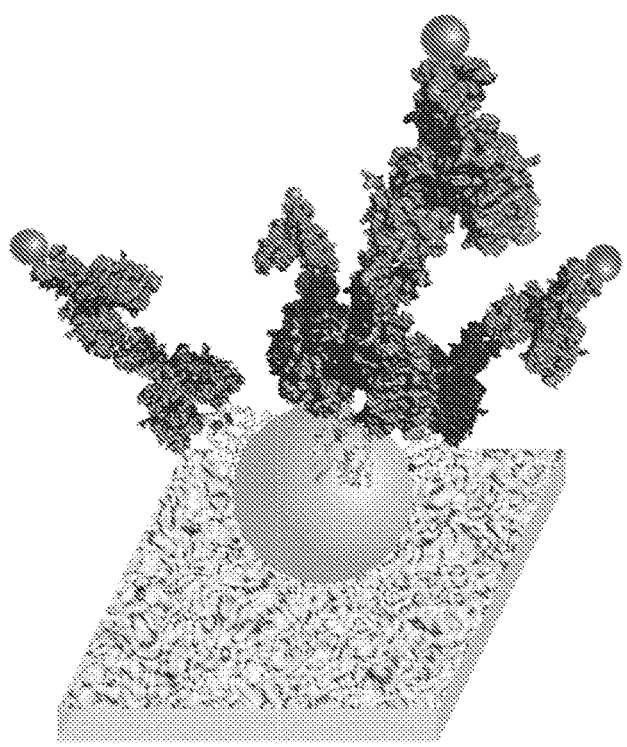
FIG. 2A-2B illustrates PLR-ZnT8 immobilized on pGOLD for ZnT8A detection. (A) A schematic of PLR-ZnT8 immobilized on pGOLD for ZnT8A detection. The substrate, purple spheres, cyan ribbons, red spheres, yellow spheres, and green or blue autoantibody represent pGOLD, liposomes, full-length ZnT8, IRDye800 fluorophores, secondary antibody anti-human IgG, and ZnT8A binding to the extracellular or intracellular surface of full-length ZnT8, respectively. (B) Scattering plot and ROC analysis of ZnT8A level detected by PLR-ZnT8 immobilized on pGOLD for 140 human sera from 50 T1D patients and 90 healthy individuals provided by IASP: ~76% sensitivity and ~95% specificity.

Previously the inventors developed a plasmonic gold substrate for near-infrared fluorescence enhanced (NIR-FE) biological detections, and performed a pilot study of T1D autoantibody assay using a small number of human sera and whole blood such as finger-prick samples[10]. Here we adopted this pGOLD (from Nirmidas Biotech. Inc) platform to evaluate the ability of PLR-ZnT8 for ZnT8A detection in hundreds of human serum samples. For simply printed PLR-ZnT8 on a pGOLD slide, proteoliposomes presented a large number of full-length ZnT8 free of direct contact or interactions with the gold surface, efficiently maintaining the proper folding of full-length ZnT8 and thus enabling auto-reactive sites accessible to ZnT8A. The gold nano-islands structure on pGOLD were arranged in such a way that the edges of adjacent islands conformed to each other for the generation of abundant nano-gaps that supported strong electric field enhancement. This and surface plasmonic resonance coupling with NIR fluorophore excited states afforded increased radiative emission and thus fluorescence enhancement by ~100-fold[10], boosting the sensitivity of the NIR-based bio-assay. PLR-ZnT8 immobilized on pGOLD (PLR-ZnT8/pGOLD) was used to capture ZnT8A in human serum samples diluted by 20-fold with fetal bovine serum (FBS), and the captured autoantibody was subsequently labeled with NIR fluorophore-conjugated secondary antibody (i.e., anti-human IgG-IRDye800). The amounts of ZnT8A were then analyzed through the fluorescence intensity of the fluorophore (FIG. 2A).

Figure 2B:
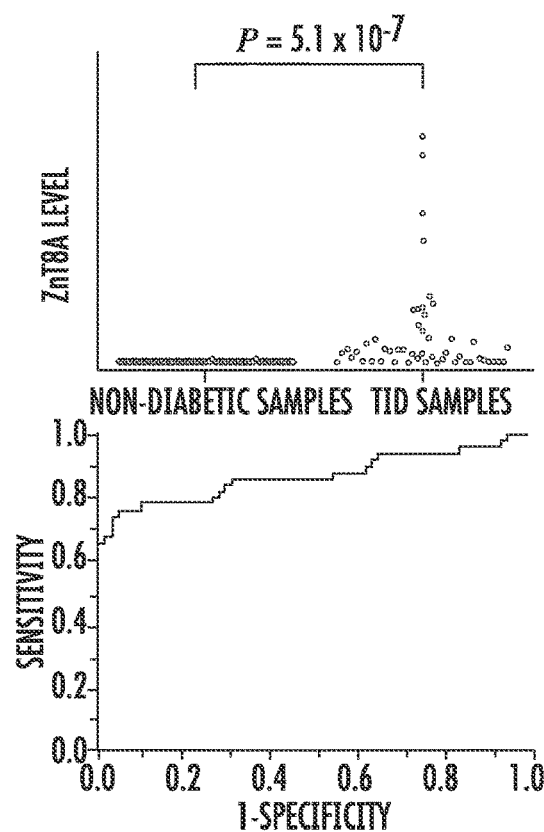

First, the inventors participated in the 2016 Islet Autoantibody Standardization Program (IASP) workshop to evaluate the ability of PLR-ZnT8/pGOLD for ZnT8A detection. For 140 human sera from 50 T1D patients and 90 healthy individuals, PLR-ZnT8/pGOLD achieved 66% sensitivity and ~100% specificity by blind tests. The assay performance can be adjusted to ~76% sensitivity and ~95% by lowering the cutoff according to the receiver operating characteristic (ROC) curve analysis (FIG. 2B, $P=5.0\times10^{-7}$). These results outperformed ZnT8A detection using a single variant of CTD, and matched the best ZnT8A detection using two variants of CTD based on other methods (i.e., radioimmunoassay, luciferase immunoprecipitation systems, and enzyme-linked immunosorbent assay) among all participating assays in the 2016 IASP workshop (Table S1 in the Supporting Information).

Subsequently another set of 167 human sera from 88 T1D patients and 79 healthy individuals provided by University of Florida were combined with sera samples from IASP to form a large number of samples for further evaluation of ZnT8A detection by PLR-ZnT8/pGOLD (i.e., 307 human sera in total, including 138 T1D and 169 non-diabetic sera). With this combined serum set, our PLR-ZnT8/pGOLD assay still achieved ~76% sensitivity and ~97% specificity, effectively discriminating T1D samples from non-diabetic samples (FIG. 3, $P=4.2\times10^{-22}$) and making it one of the best ZnT8A assays among previously reported ones[2,17]. To confirm the reproducibility of our PLR-ZnT8/pGOLD assay, the inventors repeated the serum screening twice and found good correlation between two sets of measurements of ZnT8A ($R^2=0.87$, FIG. S2 in the Supporting Information).

Figure 3:
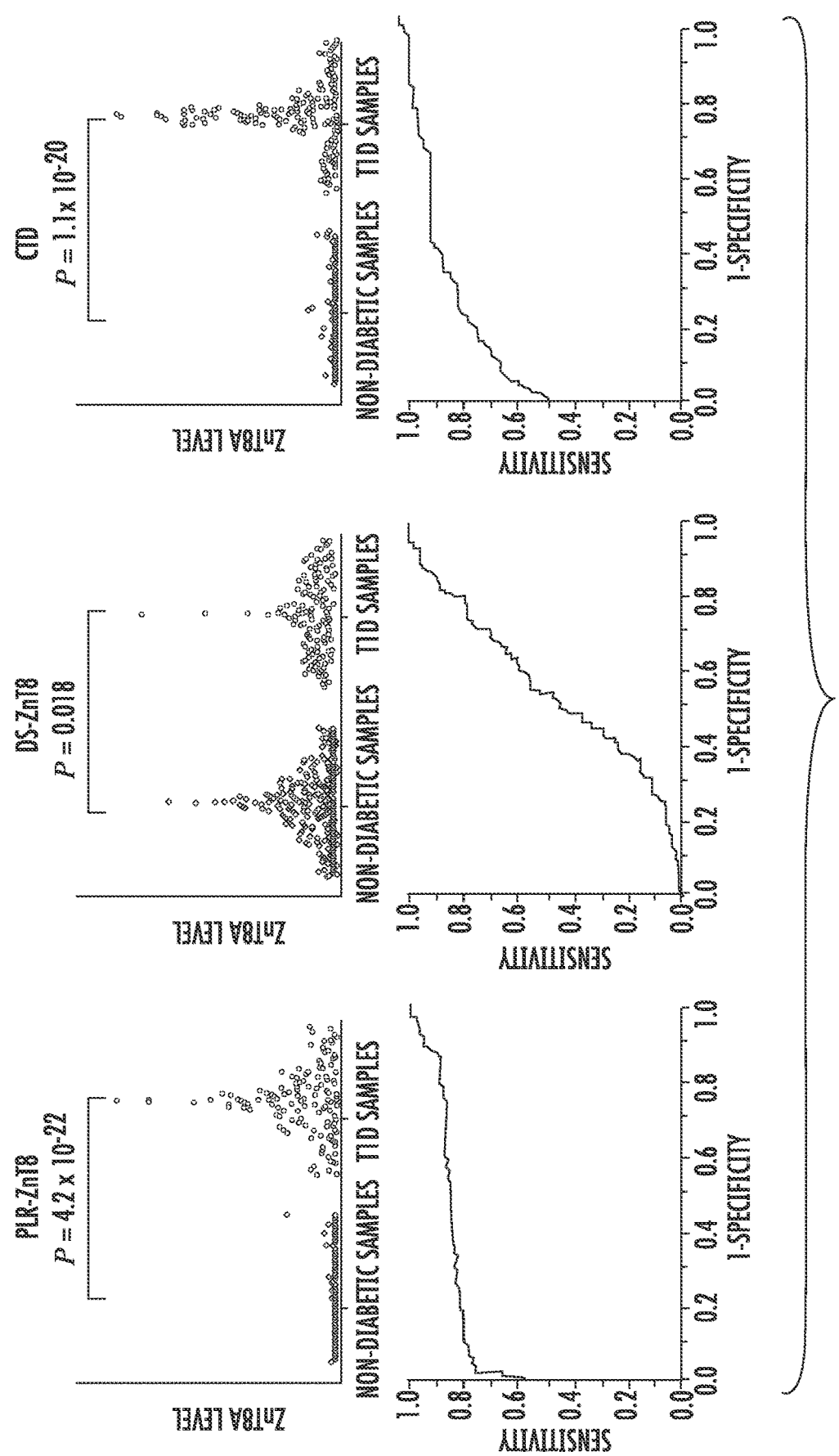
FIG. 3 illustrates the superiority of PLR-ZnT8 immobilized on pGOLD for ZnT8A detection. Scattering plot and ROC analysis of ZnT8A level detected by different ZnT8-related antigens immobilized on pGOLD for 307 human sera from 138 T1D patients and 169 healthy individuals provided by IASP and University of Florida: assay performance of PLR-ZnT8 was ~76% sensitivity and ~97% specificity; assay performance of DS-ZnT8 was ~2% sensitivity and ~94% specificity; assay performance of CTD was ~59% sensitivity and 95% specificity. All used antigens were the 325R variant.

For comparison, DS-ZnT8 and CTD were also immobilized on pGOLD in parallel with PLR-ZnT8 (unless otherwise mentioned, all ZnT8 related antigens we used were the 325R variant). Under the same experimental conditions, DS-ZnT8 did not afford useful ZnT8A detection ability presumably due to the loss of structural integrity during the assay, while CTD provided ~17% lower sensitivity than that of PLR-ZnT8 (FIG. 3). The ROC curve analysis of ZnT8A level detected by PLR-ZnT8 revealed that area under the curve (AUC) was 0.85, greater than 0.77 and 0.51 for the cases of CTD and DS-ZnT8, respectively (FIG. 3). Further correlation analysis of ZnT8A level detected by PLR-ZnT8 and CTD showed that the detection behavior of ZnT8A between PLR-ZnT8 and CTD was discrepant ($R^2=0.45$, FIG. S3 in the Supporting Information), implying PLR-ZnT8 contained more auto-reactive sites accessible to ZnT8A, leading to the improved sensitivity. Lastly, the AUC value was ~0.5 for the case of ZnT8A detection by ZnT8-free liposomes, indicating that liposomes minimally contributed to ZnT8A detection (FIG. S4 in the Supporting information).

For simplex ZnT8A assay, compared to conventional ZnT8A detection methods (e.g., enzyme-linked immunosorbent assay[18], radioimmuoassay[19], electrochemiluminescence[20], luciferase immunoprecipitation systems[21]), our PLR-ZnT8/pGOLD assay developed here demonstrated improved sensitivity and specificity (~76% sensitivity and ~97% specificity for 307 human serum samples), rapid assay process (~4 h), low sample volume requirement (5 μL), and low cost (10 dollars per sample) (See Methods for detailed experimental procedures).

Multiplexed Detection of Autoantibodies Towards T1D Diagnosis

In addition to PLR-ZnT8, we also performed simultaneous detection of IA2A and GADA using robotically printed microarrays of IA2 (fragments encompassing 604-979 aa from Kronus Inc.) and GAD (recombinant protein from Diamyd Medical Inc.) antigens, which were two additional major biomarkers for T1D diagnosis. After incubation with 5 μL human serum diluted by 100 μL FBS, washing away excess biomolecules and labeling with anti-human IgG-IRDye800 conjugates, autoantibodies captured by corresponding antigens were quantified based on the fluorescence intensity.

Figure 4A:
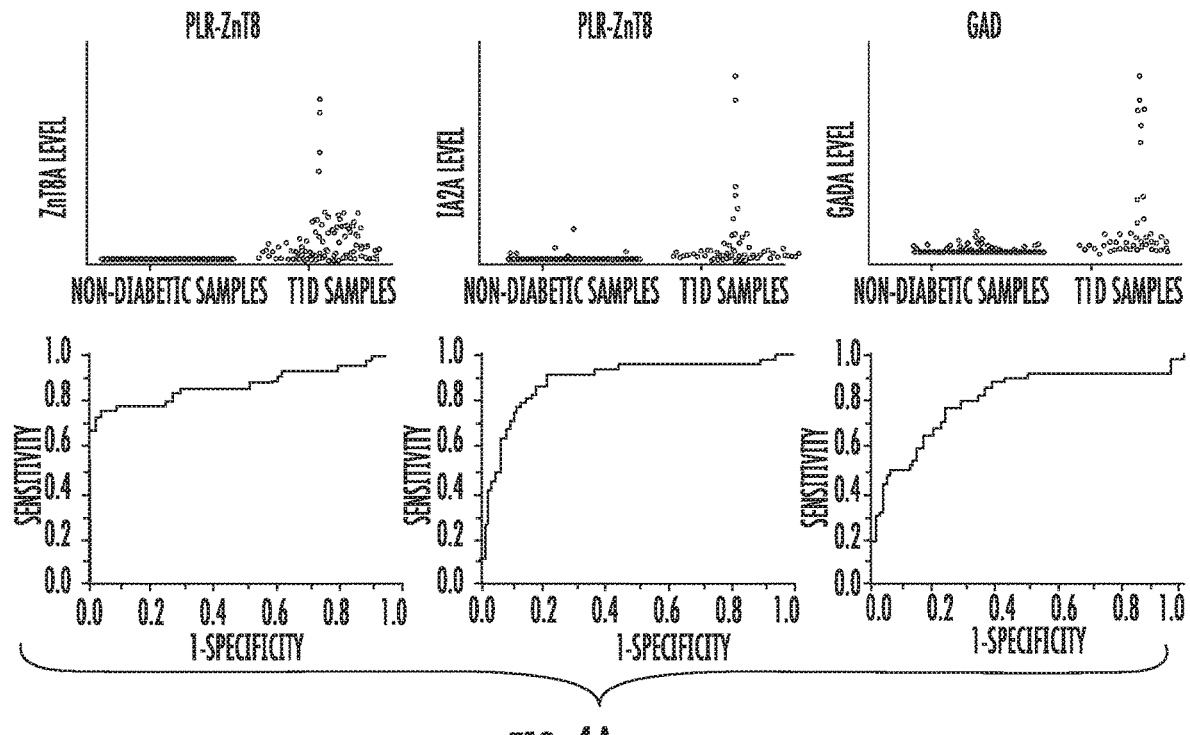
FIG. 4A-4B illustrates multiplexed detection of autoantibodies for T1D diagnosis. (A) Scattering plot and ROC analysis of ZnT8A, IA2A, and GADA level detected by pGOLD-based microarray for 140 human sera from 50 T1D patients and 90 healthy individuals provided by IASP: ~76% sensitivity and ~95% specificity for the PLR-ZnT8 case; ~68% sensitivity and ~92% specificity for the IA2A case; ~50% sensitivity and 94% specificity for the GADA case. (B) Scattering plot and ROC analysis of ZnT8A, IA2A, and GADA level detected by pGOLD-based microarray for 307 human sera from 138 T1D patients and 169 healthy individuals provided by IASP and University of Florida: ~76% sensitivity and ~97% specificity for the PLR-ZnT8 case; ~71% sensitivity and ~95% specificity for the IA2A case; ~40% sensitivity and ~95% specificity for the GADA case.
Figure 4B:
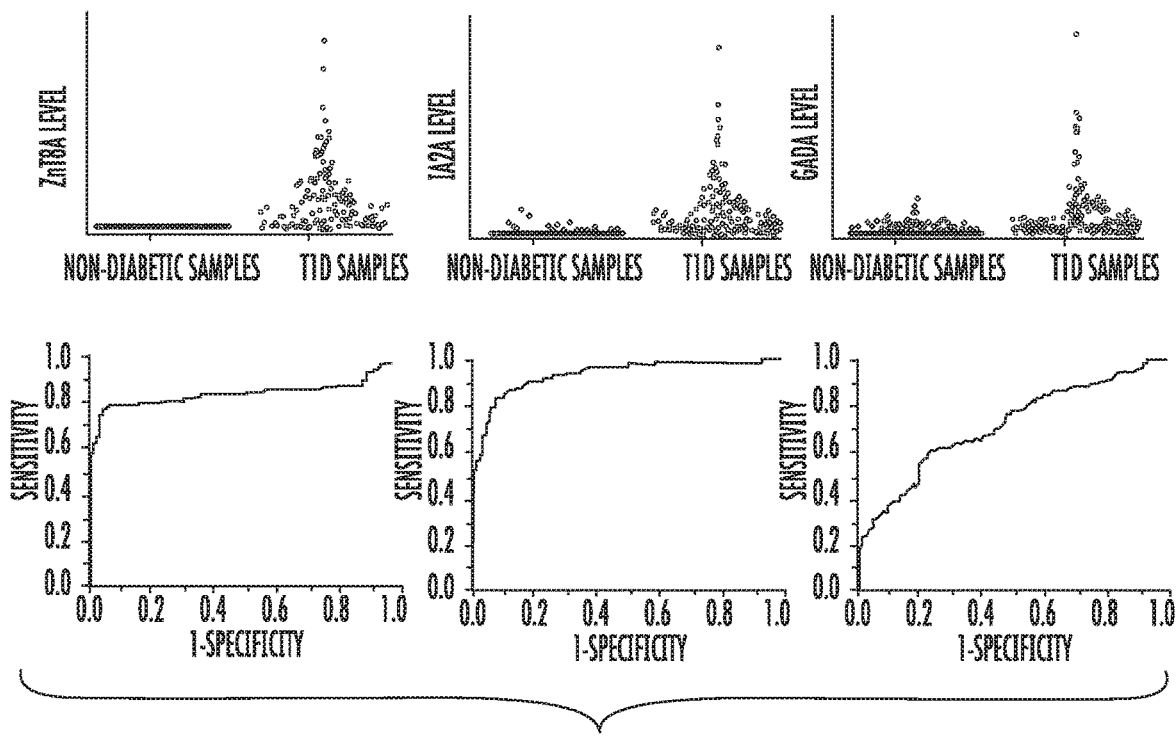
Figures 5A, 5B:
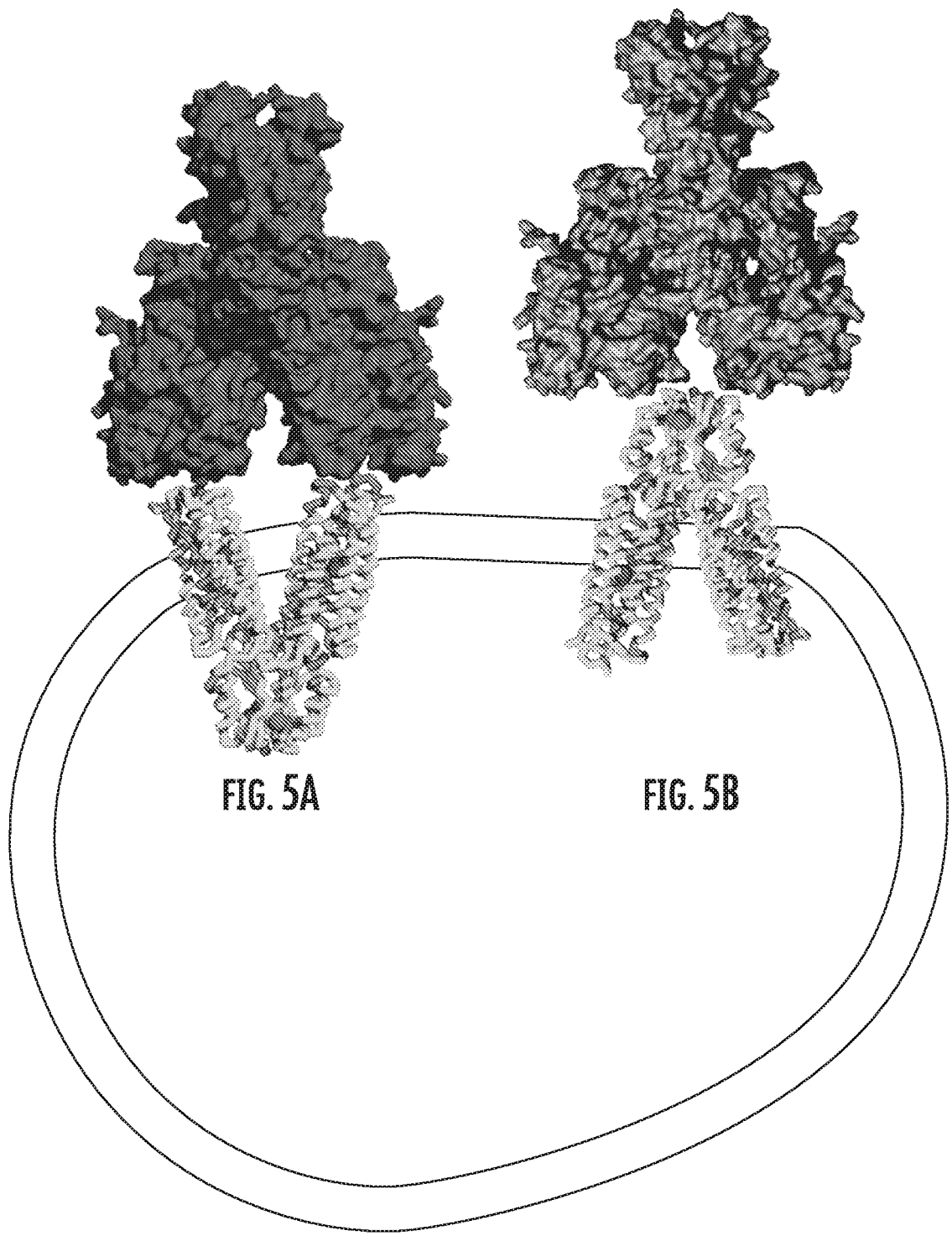
FIG. 5 illustrates a liposome of the present invention comprising two full length ZnT8 proteins. A. The transmembrane domain (TMD) of a ZnT8 protein is expressed on the exterior of the liposome having its apex (or C-terminal domain, CTD) in the center of the liposome. A ZnT8 antibody directed to the TMD is shown in blue. B. The cytosolic C-terminal domain (CTD) or apex of a ZnT8 protein is expressed on the exterior of the liposome having its TMD on the interior of the liposome. A ZnT8 antibody directed to the CTD is shown in green.

For samples from IASP (i.e., 50 T1D and 90 non-diabetics sera), we obtained ~68% sensitivity and ~92% specificity for IA2A detection, and a relatively poor ~50% sensitivity and ~94% specificity for GADA detection (FIG. 4A). For the combined IASP samples and those from University of Florida (i.e., 307 human sera including 138 T1D and 169 non-diabetic sera), detection performance of IA2A still achieved 71% sensitivity and ~95% specificity, but with only ~40% sensitivity and ~95% specificity for GADA detection (FIG. 4B). Including the PLR-ZnT8 detection results, the combination of the three kinds of autoantibodies with this large sample set gave an assay performance of ~89% sensitivity and 93% specificity for T1D diagnosis. Clearly, much room existed for improving GADA assay on our platform. Given their high prevalence, ZnT8A obviously overlapped with GADA and IA2A at disease onset[2]. Analyzed in terms of the levels of reactivity, ZnT8A correlated weakly with GADA ($R^2=0.19$, FIG. S5 in the Supporting Information) and moderately with IA2A ($R^2=0.46$, FIG. S5 in the Supporting Information), indicating ZnT8A was likely an independent T1D biomarker in agreement with previous literatures[2].

ZnT8A is thought to be conformation specific, mainly recognizing the ZnT8 self-antigen in its native conformation. Purification of multi-spanning full-length ZnT8 requires detergent solubilization, but the lack of structural stability of DS-ZnT8 poses a major challenge to maintain the proper folding of conformational epitopes. The harsh antigen handling procedures (e.g., drying, rehydration) further exacerbate the loss of bio-activity when full-length ZnT8 is immobilized on pGOLD. To overcome these limitations, after a series of optimization efforts, the inventors developed a proteoliposome-based approach that can dramatically improve the structural stability and proper folding of full-length ZnT8 in a protective lipid matrix, rendering auto-reactive sites accessible to ZnT8A with high bio-activity[13]. Even under strict drying and rehydration experimental conditions, a majority of full-length ZnT8 in PLR-ZnT8 still remain intact, in sharp contrast to a complete loss of structural integrity of full-length ZnT8 in DS-ZnT8 under identical experimental conditions.

According to literature, the main ZnT8A detected by CTD were the ones released from beta-cells after their destruction, revealing a late stage of T1D. In this regard, the detection of ZnT8A captured by CTD can validate T1D but may lack the ability to predict T1D in the earliest stages of disease. Our results suggested that the PLR-ZnT8 may provide additional auto-reactive sites outside of CTD to capture more ZnT8A, contributing to an improved assay sensitivity. These autoantibodies are presumed to be from the extracellular matrix, which may represent the products formed in the early stages of T1D by either beta-cells or immune responses.

In sum, taking advantage of the novel structure of PLR-ZnT8, we developed an efficient microarray-based assay for T1D autoantibody detection. Proteoliposomes efficiently maintained the proper folding of full-length ZnT8, enabling ZnT8A to access auto-reactive sites. PLR-ZnT8 immobilized on pGOLD achieved ZnT8A detection performance of ~76% sensitivity with ~97% specificity for 307 human sera from 138 T1D patients and 169 healthy individuals, superior to those of ~2% sensitivity with ~94% specificity and ~59% sensitivity with ~94% specificity based on DS-ZnT8 and CTD, respectively. Moreover, pGOLD was also applied for multiplexed detection of other T1D-related autoantibodies, IA2A and GADA from over 300 serum samples, with outcomes of ~71% sensitivity with ~95% specificity and ~40% sensitivity with ~95% specificity, respectively; leading to an overall multiplex assay performance of ~89% sensitivity with ~93% specificity by assessing the three kinds of autoantibodies combined.

Our current work established proteoliposomes on pGOLD as a promising platform for ZnT8A detection with high sensitivity and specificity. A future direction is to improve GADA detection and optimize the overall performance of multiplexed assay for screening presymptomatic T1D in at-risk populations. Diagnosing the disease at earlier stages will provide safe and effective therapeutic options for prevention.

Kits of the Disclosure

Any of the compositions described herein may be comprised in a kit. In a non-limiting example, a proteoliposome having an interior and an exterior comprising a ZnT8 protein with a cytosolic domain exposed on the exterior of the proteoliposomes, such as PLR-ZnT8, may be comprised in a kit.

The kits may comprise a suitably aliquoted of a proteoliposomes comprising ZnT8 of the present invention, such as PLR-ZnT8, and, in some cases, one or more additional agents, such as a chip or captured autoantibodies that binds to antibodies targeting ZnT8, as an examples. The component(s) of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing proteoliposomes comprising ZnT8 of the present invention and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means.

METHODS/EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Methods

Materials.

Hyclone fetal bovine serum (FBS) was purchased from Fisher Chemicals. IRDye800-NHS ester was purchased from Licor Biosciences. GAD65 was purchased from Diamyd Medical and IA2 (ICA512) was purchased from Kronus Inc. Goat anti-human IgG antibody was purchased from Vector Lab. Plasmonic gold chips (pGOLD) were purchased from Nirmidas Inc. Human serum Institutional Review Board approval for this study was obtained from Stanford University. And human serum samples were provided from University of Florida and Islet Autoantibody Standardization Program (IASP). Samples were aliquoted and stored at −80° C. until processing.

Protein Sequences.

Below are examples of four ZnT8 protein sequences used in the present invention. Two of them are an "a" form, and two of them are a "b" form. Both the "a" form and the "b" form have the R325W variant. The Wild Type ZnT8 protein is R325, which is based on the "a" form. The W325 form is a variant.

WT, ZnT8a form R325:
(SEQ ID NO: 1)
*MEFLERTYLVNDKAAKMYAFTLESVELQQKPVNKDQCPRERPEELESGG*

MYHCHSGSKPTEKGANEYAYAKWKLCSASAICFIFMIAEVVGGHIAGSL

AVVTDAAHLLIDLTSFLLSLFSLWLSSKPPSKRLTFGWHRAEILGALLS

ILCIWVVTGVLVYLACERLLYPDYQIQATVMIIVSSCAVAANIVLTVVL

HQRCLGHNHKEVQANASVRAAFVHALGDLFQSISVLISALIIYFKPEYK

IADPICTFIFSILVLASTITILKDFSILLMEGVPKSLNYSGVKELILAV

-continued

DGVLSVHSLHIWSLTMNQVILSAHVATAASRDSQVVRREIAKALSKSFT

MHSLTIQMESPVDQDPDCLFCEDPCD

ZnT8a form W325:
(SEQ ID NO: 2)
*MEFLERTYLVNDKAAKMYAFTLESVELQQKPVNKDQCPRERPEELESGG*

MYHCHSGSKPTEKGANEYAYAKWKLCSASAICFIFMIAEVVGGHIAGSL

AVVTDAAHLLIDLTSFLLSLFSLWLSSKPPSKRLTFGWHRAEILGALLS

ILCIWVVTGVLVYLACERLLYPDYQIQATVMIIVSSCAVAANIVLTVVL

HQRCLGHNHKEVQANASVRAAFVHALGDLFQSISVLISALIIYFKPEYK

IADPICTFIFSILVLASTITILKDFSILLMEGVPKSLNYSGVKELILAV

DGVLSVHSLHIWSLTMNQVILSAHVATAASWDSQVVRREIAKALSKSFT

MHSLTIQMESPVDQDPDCLFCEDPCD

WT, ZnT8b form R325:
(SEQ ID NO: 3)
MYHCHSGSKPTEKGANEYAYAKWKLCSASAICFIFMIAEVVGGHIAGSL

AVVTDAAHLLIDLTSFLLSLFSLWLSSKPPSKRLTFGWHRAEILGALLS

ILCIWVVTGVLVYLACERLLYPDYQIQATVMIIVSSCAVAANIVLTVVL

HQRCLGHNHKEVQANASVRAAFVHALGDLFQSISVLISALIIYFKPEYK

IADPICTFIFSILVLASTITILKDFSILLMEGVPKSLNYSGVKELILAV

DGVLSVHSLHIWSLTMNQVILSAHVATAASRDSQVVRREIAKALSKSFT

MHSLTIQMESPVDQDPDCLFCEDPCD

ZnT8b form W325:
(SEQ ID NO: 4)
MYHCHSGSKPTEKGANEYAYAKWKLCSASAICFIFMIAEVVGGHIAGSL

AVVTDAAHLLIDLTSFLLSLFSLWLSSKPPSKRLTFGWHRAEILGALLS

ILCIWVVTGVLVYLACERLLYPDYQIQATVMIIVSSCAVAANIVLTVVL

HQRCLGHNHKEVQANASVRAAFVHALGDLFQSISVLISALIIYFKPEYK

IADPICTFIFSILVLASTITILKDFSILLMEGVPKSLNYSGVKELILAV

DGVLSVHSLHIWSLTMNQVILSAHVATAASWDSQVVRREIAKALSKSFT

MHSLTIQMESPVDQDPDCLFCEDPCD

Preparation of Recombinant Antigens.

The 325R polymorphic variant of human ZnT8 isoform-2 was over-expressed in HEK293 cells, and purified in reconstituted proteoliposomes as described previously. Briefly, full-length ZnT8 was solubilized by n-dodecyl β-D-maltoside (DDM), partially purified via Ni-NTA affinity to a C-terminal polyhistidine tag, and then further purified by reconstitution into proteoliposomes (the lipids containing 1,2-dioleoyl-sn-glycero-3-phosphocholine, 1,2-dioleoyl-sn-glycero-3-phospho-(1'-rac-glycerol), and 1,2-dioleoyl-sn-glycero-3-phosphoethanolamine at a ratio of 2:1:1 were premixed, dried, sonicated and detergent destabilized with DDM before reconstitution of full-length ZnT8) followed by proteoliposome washing with a detergent-free assay buffer (20 mM HEPES, 100 mM NaCl, 1 mM TCEP, pH 7.0). The C-terminal domain (275-369 aa) of the 325R variant was His-tagged, over-expressed in HEK293 cells, and Ni-NTA affinity purified, followed by dialysis against the assay buffer. Purified full-length ZnT8 in proteoliposomes were suspended in the same assay buffer. Full-length ZnT8 in detergent micelles were prepared by solubilizing proteoliposomes with 0.1% DDM in the assay buffer. The purified full-length ZnT8, either in detergent micelles or proteoliposomes, was analyzed by SDS-PAGE with Coomassie blue staining.

HPLC Analysis of Vacuum-Dried Full-Length ZnT8.

Purified full-length ZnT8 either in detergent micelles or proteoliposomes was dried by nitrogen gas evaporation, or then kept under a vacuum for over 60 min to remove a trace amount of liquids. The completely dried full-length ZnT8 samples were rehydrated by adding ddH$_2$O with 0.1% lauryl maltose-neopentyl glycol (LMNG) and 0.1 mM fluorescein-5-maleimide (FM), a thiol-reactive fluorescence label. Unreacted FM was removed by passing the rehydrated mixture through a desalting column pre-equilibrated with the assay buffer. The resultant LMNG-solubilized and FM-labeled full-length ZnT8 were analyzed by size-exclusion HPLC using the FM fluorescence readout to facilitate the detection of full-length ZnT8 and lipids. An aliquot of proteoliposome suspension or DS-ZnT8 in the assay buffer was HPLC-analyzed in parallel as a control.

Preparation of T1D-Related Antigens Microarray on pGOLD.

As-prepared PLR-ZnT8 (0.2 mg/mL), IA2 (0.088 mg/mL), and GAD (0.13 mg/mL) antigens were printed onto pGOLD using GeSiM Nano-Plotter 2.1. Each microarray consisted of three spots of PLR-ZnT8, IA2, and GAD antigens. ~5 nL of antigen solution was delivered to each spot. Microarray followed a 3×3 layout. Spot diameter was ~400 µm and the distance between each spot was ~1000 µm. 16 identical microarrays were formed on each pGOLD. The prepared pGOLD were vacuum-sealed and stored at −20° C. before use. In a different microarray preparation process, as-prepared DS-ZnT8 and CTD were also immobilized on pGOLD under the same experimental conditions with PLR-ZnT8 for antibody detection.

Multiplexed Detection of T1D-Related Autoantibodies.

The prepared pGOLD was integrated in a module in which 16 identical microarrays on each biochip were separated into 16 wells to process 16 samples. Each well was incubated with 5 µL human serum diluted with 100 µL FBS (20-fold) for 1.5 h, followed by incubation with anti-human IgG-IRDye800 conjugates at the final concentration of 4 nM diluted by FBS for 45 min. Each well was washed with washing buffer between each incubation procedure. 14 samples, together with two reference samples (one serum sample, IgG positive for GAD, and one serum sample with negative IgG binding to all T1D-related antigens) were applied to each biochip. The assay system was composed of the printed antigen array on a pGOLD slide, slide frame, buffers, plate washer and a dual-channel (700/800 nm) scanner, which can be easily deployed in clinical and public-health laboratories.

Data Analysis.

After the assay process, each biochip was scanned with a MidaScan-IR near-infrared scanner. MidaScan-IR is a dual channel (700 and 800 nm) near-infrared confocal microscope scanner for imaging tissues, cells and microarrays on standard glass or plasmonic slides. IRDye680 and IRDye800 fluorescence images were generated, and the median fluorescence signal for each channel on each microarray spot was quantified by MidaScan software. For each sample, each antigen and each channel, the average of the three median fluorescence signals for three spots was calculated and normalized by reference samples through a two-point calibration. On each pGOLD we added one T1D positive sample to be used as the reference for normalization of other samples' MFI signal to attenuate the difference caused by experimental conditions. Cutoff was determined by the ROC curve analysis. Measurements were performed three times for all values presented in this work.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of detecting ZnT8 antibodies in serum comprising:
   (a) providing a collection of proteoliposomes having an interior and an exterior wherein some proteoliposomes have protein sequences of a transmembrane domain (TMD) of a zinc transporter 8 (ZnT8) on its exterior and other proteoliposomes comprise protein sequences of a cytosolic domain (CTD) of a ZnT8 protein exposed on its exterior,
   wherein the protein sequences of a TMD and a CTD are part of a full length ZnT8 protein,
   wherein the full length ZnT8 protein is a 325R polymorphic variant of human ZnT8,
   wherein the collection of proteoliposomes is prepared by dehydrating soluble ZnT8-containing proteoliposomes followed by rehydration of the dehydrated ZnT8-containing proteoliposomes, and
   wherein the collection of proteoliposomes is bound to a plate or chip;
   (b) adding serum comprising antibodies targeting the protein sequences of TMD and/or CTD forming proteoliposomes bound to the antibodies;
   (c) adding a labelled secondary antibody that binds to the antibodies bound to the proteoliposomes; and
   (d) measuring the amount of antibodies targeting the protein sequences of TMD and/or CTD bound to the proteoliposomes.

2. The method of claim 1 wherein the collection of proteoliposomes comprises inside out proteoliposomes and right side out proteoliposomes.

3. The method of claim 2 wherein inside out proteoliposomes comprise CTD protein sequences on its exterior.

4. The method of claim 2 wherein the right side out proteoliposomes comprise TMD protein sequences on its exterior.

5. The method of claim 1, wherein the collection of proteoliposomes is printed on the chip.

6. The method of claim 5, wherein the chip is a plasmonic gold (pGOLD) chip.

7. The method of claim 6 comprising one or more secondary proteins bound to the chip.

8. The method of claim 7 wherein the one or more secondary proteins is selected from the group consisting of islet antigen 2 (IA2), glutamic acid decarboxylase (GAD), and a combination thereof.

9. The method of claim 1 wherein the serum is human.

10. The method of claim 9 wherein the human serum is diluted with fetal bovine serum (FBS).

11. The method of claim 10 wherein the human serum is diluted in the range of 10 to 30 fold with the fetal bovine serum (FBS).

12. The method of claim 1 wherein the labelled secondary antibody comprises a fluorescent label.

13. The method of claim 12, wherein the measuring comprises determining the amount of the antibodies bound to the ZnT8 protein by analyzing the fluorescence intensity of the fluorescent label.

14. The method of claim 11, wherein the measuring the antibodies bound to the ZnT8 protein comprises an infrared scanner.

15. The method of claim 1 wherein the collection of proteoliposomes comprises lipids selected from the group consisting of 1,2-dioleoyl-sn-glycero-3-phophocholine; 1,2-dioleoyl-sn-glycero-3-phospho-(1'-rac-glycerol); 1,2-dioleoyl-sn-glycero-3-phophoethaolamine; and a combination thereof.

16. The method of claim 1 wherein the detection has a detection performance of greater than 70% sensitivity and greater than 90% specificity.

* * * * *

SEQUENCE LISTING

<160> NUMBER OF SEQ ID NOS: 4

<210> SEQ ID NO 1
<211> LENGTH: 369
<212> TYPE: PRT
<213> ORGANISM: Homo sapiens

<400> SEQUENCE: 1

```
Met Glu Phe Leu Glu Arg Thr Tyr Leu Val Asn Asp Lys Ala Ala Lys
1               5                   10                  15

Met Tyr Ala Phe Thr Leu Glu Ser Val Glu Leu Gln Gln Lys Pro Val
            20                  25                  30

Asn Lys Asp Gln Cys Pro Arg Glu Arg Pro Glu Glu Leu Glu Ser Gly
        35                  40                  45

Gly Met Tyr His Cys His Ser Gly Ser Lys Pro Thr Glu Lys Gly Ala
    50                  55                  60

Asn Glu Tyr Ala Tyr Ala Lys Trp Lys Leu Cys Ser Ala Ser Ala Ile
65                  70                  75                  80

Cys Phe Ile Phe Met Ile Ala Glu Val Val Gly Gly His Ile Ala Gly
                85                  90                  95

Ser Leu Ala Val Val Thr Asp Ala Ala His Leu Leu Ile Asp Leu Thr
            100                 105                 110

Ser Phe Leu Leu Ser Leu Phe Ser Leu Trp Leu Ser Ser Lys Pro Pro
        115                 120                 125

Ser Lys Arg Leu Thr Phe Gly Trp His Arg Ala Glu Ile Leu Gly Ala
    130                 135                 140

Leu Leu Ser Ile Leu Cys Ile Trp Val Val Thr Gly Val Leu Val Tyr
145                 150                 155                 160

Leu Ala Cys Glu Arg Leu Leu Tyr Pro Asp Tyr Gln Ile Gln Ala Thr
                165                 170                 175

Val Met Ile Ile Val Ser Ser Cys Ala Val Ala Ala Asn Ile Val Leu
            180                 185                 190

Thr Val Val Leu His Gln Arg Cys Leu Gly His Asn His Lys Glu Val
        195                 200                 205

Gln Ala Asn Ala Ser Val Arg Ala Ala Phe Val His Ala Leu Gly Asp
    210                 215                 220
```

-continued

```
Leu Phe Gln Ser Ile Ser Val Leu Ile Ser Ala Leu Ile Ile Tyr Phe
225                 230                 235                 240

Lys Pro Glu Tyr Lys Ile Ala Asp Pro Ile Cys Thr Phe Ile Phe Ser
                245                 250                 255

Ile Leu Val Leu Ala Ser Thr Ile Thr Ile Leu Lys Asp Phe Ser Ile
            260                 265                 270

Leu Leu Met Glu Gly Val Pro Lys Ser Leu Asn Tyr Ser Gly Val Lys
        275                 280                 285

Glu Leu Ile Leu Ala Val Asp Gly Val Leu Ser Val His Ser Leu His
    290                 295                 300

Ile Trp Ser Leu Thr Met Asn Gln Val Ile Leu Ser Ala His Val Ala
305                 310                 315                 320

Thr Ala Ala Ser Arg Asp Ser Gln Val Val Arg Arg Glu Ile Ala Lys
                325                 330                 335

Ala Leu Ser Lys Ser Phe Thr Met His Ser Leu Thr Ile Gln Met Glu
            340                 345                 350

Ser Pro Val Asp Gln Asp Pro Asp Cys Leu Phe Cys Glu Asp Pro Cys
        355                 360                 365

Asp
```

<210> SEQ ID NO 2
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Met Glu Phe Leu Glu Arg Thr Tyr Leu Val Asn Asp Lys Ala Ala Lys
1               5                   10                  15

Met Tyr Ala Phe Thr Leu Glu Ser Val Glu Leu Gln Gln Lys Pro Val
            20                  25                  30

Asn Lys Asp Gln Cys Pro Arg Glu Arg Pro Glu Glu Leu Glu Ser Gly
        35                  40                  45

Gly Met Tyr His Cys His Ser Gly Ser Lys Pro Thr Glu Lys Gly Ala
    50                  55                  60

Asn Glu Tyr Ala Tyr Ala Lys Trp Lys Leu Cys Ser Ala Ser Ala Ile
65                  70                  75                  80

Cys Phe Ile Phe Met Ile Ala Glu Val Val Gly Gly His Ile Ala Gly
                85                  90                  95

Ser Leu Ala Val Val Thr Asp Ala Ala His Leu Leu Ile Asp Leu Thr
            100                 105                 110

Ser Phe Leu Leu Ser Leu Phe Ser Leu Trp Leu Ser Ser Lys Pro Pro
        115                 120                 125

Ser Lys Arg Leu Thr Phe Gly Trp His Arg Ala Glu Ile Leu Gly Ala
    130                 135                 140

Leu Leu Ser Ile Leu Cys Ile Trp Val Val Thr Gly Val Leu Val Tyr
145                 150                 155                 160

Leu Ala Cys Glu Arg Leu Leu Tyr Pro Asp Tyr Gln Ile Gln Ala Thr
                165                 170                 175

Val Met Ile Ile Val Ser Ser Cys Ala Val Ala Ala Asn Ile Val Leu
            180                 185                 190

Thr Val Val Leu His Gln Arg Cys Leu Gly His Asn His Lys Glu Val
        195                 200                 205
```

Gln Ala Asn Ala Ser Val Arg Ala Ala Phe Val His Ala Leu Gly Asp
    210                 215                 220

Leu Phe Gln Ser Ile Ser Val Leu Ile Ser Ala Leu Ile Ile Tyr Phe
225                 230                 235                 240

Lys Pro Glu Tyr Lys Ile Ala Asp Pro Ile Cys Thr Phe Ile Phe Ser
            245                 250                 255

Ile Leu Val Leu Ala Ser Thr Ile Thr Ile Leu Lys Asp Phe Ser Ile
            260                 265                 270

Leu Leu Met Glu Gly Val Pro Lys Ser Leu Asn Tyr Ser Gly Val Lys
        275                 280                 285

Glu Leu Ile Leu Ala Val Asp Gly Val Leu Ser Val His Ser Leu His
        290                 295                 300

Ile Trp Ser Leu Thr Met Asn Gln Val Ile Leu Ser Ala His Val Ala
305                 310                 315                 320

Thr Ala Ala Ser Trp Asp Ser Gln Val Val Arg Arg Glu Ile Ala Lys
            325                 330                 335

Ala Leu Ser Lys Ser Phe Thr Met His Ser Leu Thr Ile Gln Met Glu
            340                 345                 350

Ser Pro Val Asp Gln Asp Pro Asp Cys Leu Phe Cys Glu Asp Pro Cys
        355                 360                 365

Asp

<210> SEQ ID NO 3
<211> LENGTH: 320
<212> TYPE: PRT
<213> ORGANISM: Homo sapiens

<400> SEQUENCE: 3

Met Tyr His Cys His Ser Gly Ser Lys Pro Thr Glu Lys Gly Ala Asn
1               5                   10                  15

Glu Tyr Ala Tyr Ala Lys Trp Lys Leu Cys Ser Ala Ser Ala Ile Cys
            20                  25                  30

Phe Ile Phe Met Ile Ala Glu Val Val Gly Gly His Ile Ala Gly Ser
            35                  40                  45

Leu Ala Val Val Thr Asp Ala Ala His Leu Leu Ile Asp Leu Thr Ser
50                  55                  60

Phe Leu Leu Ser Leu Phe Ser Leu Trp Leu Ser Ser Lys Pro Pro Ser
65                  70                  75                  80

Lys Arg Leu Thr Phe Gly Trp His Arg Ala Glu Ile Leu Gly Ala Leu
            85                  90                  95

Leu Ser Ile Leu Cys Ile Trp Val Val Thr Gly Val Leu Val Tyr Leu
            100                 105                 110

Ala Cys Glu Arg Leu Leu Tyr Pro Asp Tyr Gln Ile Gln Ala Thr Val
            115                 120                 125

Met Ile Ile Val Ser Ser Cys Ala Val Ala Ala Asn Ile Val Leu Thr
        130                 135                 140

Val Val Leu His Gln Arg Cys Leu Gly His Asn His Lys Glu Val Gln
145                 150                 155                 160

Ala Asn Ala Ser Val Arg Ala Ala Phe Val His Ala Leu Gly Asp Leu
            165                 170                 175

Phe Gln Ser Ile Ser Val Leu Ile Ser Ala Leu Ile Ile Tyr Phe Lys
            180                 185                 190

Pro Glu Tyr Lys Ile Ala Asp Pro Ile Cys Thr Phe Ile Phe Ser Ile
            195                 200                 205

```
Leu Val Leu Ala Ser Thr Ile Thr Ile Leu Lys Asp Phe Ser Ile Leu
    210                 215                 220

Leu Met Glu Gly Val Pro Lys Ser Leu Asn Tyr Ser Gly Val Lys Glu
225                 230                 235                 240

Leu Ile Leu Ala Val Asp Gly Val Leu Ser Val His Ser Leu His Ile
            245                 250                 255

Trp Ser Leu Thr Met Asn Gln Val Ile Leu Ser Ala His Val Ala Thr
                260                 265                 270

Ala Ala Ser Arg Asp Ser Gln Val Val Arg Arg Glu Ile Ala Lys Ala
        275                 280                 285

Leu Ser Lys Ser Phe Thr Met His Ser Leu Thr Ile Gln Met Glu Ser
    290                 295                 300

Pro Val Asp Gln Asp Pro Asp Cys Leu Phe Cys Glu Asp Pro Cys Asp
305                 310                 315                 320
```

<210> SEQ ID NO 4
<211> LENGTH: 320
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Met Tyr His Cys His Ser Gly Ser Lys Pro Thr Glu Lys Gly Ala Asn
1               5                   10                  15

Glu Tyr Ala Tyr Ala Lys Trp Lys Leu Cys Ser Ala Ser Ala Ile Cys
            20                  25                  30

Phe Ile Phe Met Ile Ala Glu Val Val Gly Gly His Ile Ala Gly Ser
        35                  40                  45

Leu Ala Val Val Thr Asp Ala Ala His Leu Leu Ile Asp Leu Thr Ser
    50                  55                  60

Phe Leu Leu Ser Leu Phe Ser Leu Trp Leu Ser Ser Lys Pro Pro Ser
65                  70                  75                  80

Lys Arg Leu Thr Phe Gly Trp His Arg Ala Glu Ile Leu Gly Ala Leu
                85                  90                  95

Leu Ser Ile Leu Cys Ile Trp Val Val Thr Gly Val Leu Val Tyr Leu
            100                 105                 110

Ala Cys Glu Arg Leu Leu Tyr Pro Asp Tyr Gln Ile Gln Ala Thr Val
        115                 120                 125

Met Ile Ile Val Ser Ser Cys Ala Val Ala Ala Asn Ile Val Leu Thr
    130                 135                 140

Val Val Leu His Gln Arg Cys Leu Gly His Asn His Lys Glu Val Gln
145                 150                 155                 160

Ala Asn Ala Ser Val Arg Ala Ala Phe Val His Ala Leu Gly Asp Leu
                165                 170                 175

Phe Gln Ser Ile Ser Val Leu Ile Ser Ala Leu Ile Ile Tyr Phe Lys
            180                 185                 190

Pro Glu Tyr Lys Ile Ala Asp Pro Ile Cys Thr Phe Ile Phe Ser Ile
        195                 200                 205

Leu Val Leu Ala Ser Thr Ile Thr Ile Leu Lys Asp Phe Ser Ile Leu
    210                 215                 220

Leu Met Glu Gly Val Pro Lys Ser Leu Asn Tyr Ser Gly Val Lys Glu
225                 230                 235                 240

Leu Ile Leu Ala Val Asp Gly Val Leu Ser Val His Ser Leu His Ile
```

|     | 245 |     |     |     | 250 |     |     |     | 255 |     |     |
| --- | --- | --- | --- | --- | --- | --- | --- | --- | --- | --- | --- |
| Trp | Ser | Leu | Thr | Met | Asn | Gln | Val | Ile | Leu | Ser | Ala | His | Val | Ala | Thr |
|     |     |     | 260 |     |     |     |     | 265 |     |     |     |     | 270 |     |     |
| Ala | Ala | Ser | Trp | Asp | Ser | Gln | Val | Val | Arg | Arg | Glu | Ile | Ala | Lys | Ala |
|     |     | 275 |     |     |     |     | 280 |     |     |     |     | 285 |     |     |     |
| Leu | Ser | Lys | Ser | Phe | Thr | Met | His | Ser | Leu | Thr | Ile | Gln | Met | Glu | Ser |
|     | 290 |     |     |     |     | 295 |     |     |     |     | 300 |     |     |     |     |
| Pro | Val | Asp | Gln | Asp | Pro | Asp | Cys | Leu | Phe | Cys | Glu | Asp | Pro | Cys | Asp |
| 305 |     |     |     |     | 310 |     |     |     |     | 315 |     |     |     |     | 320 |